(12) United States Patent     (10) Patent No.:    US 12,629,061 B2

Peikon et al.            (45) Date of Patent:      May 19, 2026

---

(54) SPECTROMETRY SYSTEMS AND METHODS

(71) Applicant: NNOXX, INC., Seattle, WA (US)

(72) Inventors: Evan Peikon, Seattle, WA (US); Justin Saul, Seattle, WA (US); Bryan Coles, Seattle, WA (US)

(73) Assignee: NNOXX, INC., Manson, WA (US)

( * ) Notice: Subject to any disclaimer, the term of this patent is extended or adjusted under 35 U.S.C. 154(b) by 0 days.

(21) Appl. No.: 19/103,450

(22) PCT Filed: Dec. 28, 2023

(86) PCT No.: PCT/US2023/086145

§ 371 (c)(1),
(2) Date: Feb. 12, 2025

(87) PCT Pub. No.: WO2024/145419

PCT Pub. Date: Jul. 4, 2024

(65)        Prior Publication Data

US 2026/0053399 A1     Feb. 26, 2026

Related U.S. Application Data

(60) Provisional application No. 63/477,989, filed on Dec. 30, 2022.

(51) Int. Cl.
    *A61B 5/1455*       (2006.01)
    *A61B 5/00*         (2006.01)
    *A61B 5/145*        (2006.01)

(52) U.S. Cl.
CPC ...... *A61B 5/14551* (2013.01); *A61B 5/14546* (2013.01); *A61B 5/486* (2013.01); *A61B 5/742* (2013.01)

(58) Field of Classification Search
CPC . A61B 5/14551; A61B 5/14546; A61B 5/486; A61B 5/742
See application file for complete search history.

(56)        References Cited

U.S. PATENT DOCUMENTS

| | | |
|---|---|---|
| 6,922,583 B1 | 7/2005 | Perelman et al. |
| 10,080,504 B2 * | 9/2018 | Pollonini ............... A61B 5/441 |

(Continued)

FOREIGN PATENT DOCUMENTS

| | | |
|---|---|---|
| WO | WO-2022034336 A1 | 2/2022 |
| WO | WO-2022251701 A1 | 12/2022 |

OTHER PUBLICATIONS

Miura et al., "Regional difference of muscle oxygen saturation and blood volume during exercise determined by near infrared imaging device," Japanese Journal of Physiology, vol. 51, No. 5, pp. 599-606, 2001, retrieved on [Nov. 4, 2024]. Retrieved from the internet <URL: https://www.jstage.jst.go.jp/article/jjphysio 1/51/5/51_5_599/_article/-char/ja/> entire document.

(Continued)

*Primary Examiner* — Eric F Winakur
*Assistant Examiner* — Sienna C Pyle
(74) *Attorney, Agent, or Firm* — DLA Piper LLP (US)

(57)          ABSTRACT

At least one light source may be configured to illuminate a region of interest of a subject, and at least one light sensor may be configured to non-invasively measure reflected light within the region of interest. At least one processor may perform processing comprising receiving at least one measured value of light from the at least one light sensor. From the measured value of light, the processor may determine at least one thickness or depth of at least one tissue layer within the region of interest of the subject and/or perform further processing to determine at least one physical characteristic of the region of interest of the subject.

30 Claims, 26 Drawing Sheets

(56) References Cited

U.S. PATENT DOCUMENTS

| 10,219,736 | B2 | 3/2019 | Davis et al. | |
| 2014/0155760 | A1* | 6/2014 | Ridder .................. | A61B 5/443 |
| | | | | 600/479 |
| 2017/0215793 | A1 | 8/2017 | Newberry | |
| 2019/0008462 | A1 | 1/2019 | Taylor | |

OTHER PUBLICATIONS

Notification of Transmittal of the International Search Report and the Written Opinion of International Application No. PCT/US2023/086145 issued May 30, 2024, 18 pages.

\* cited by examiner

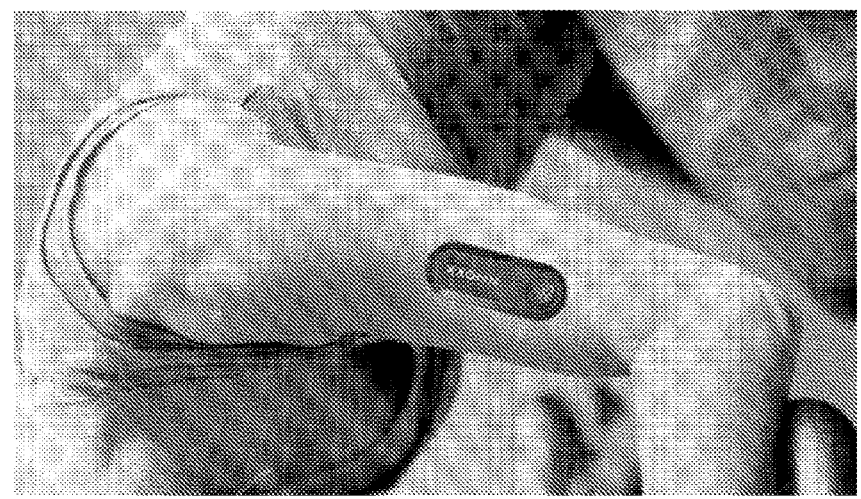
100
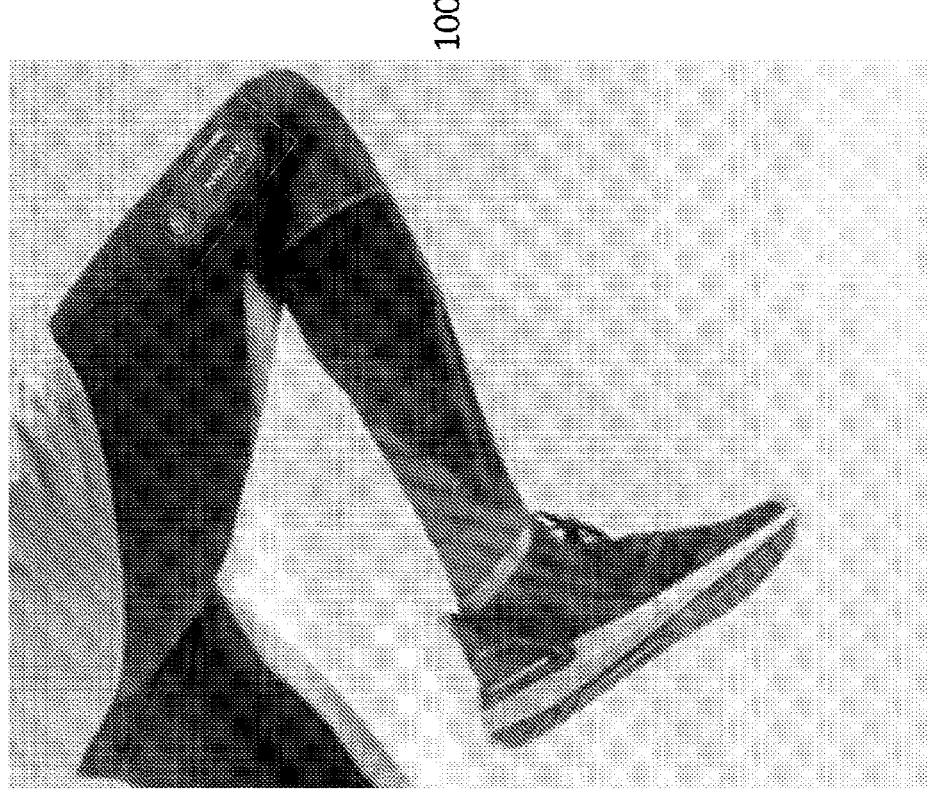
Figure 1

Figure 7   Flowchart of computational process 700 to generate biological parameters Muscle Oxygenation during a
30-second bike sprint.

Nitric oxide activity in the
blood during a 45 second
exercise bout

Internal training load during
a 45-second exercise bout

Scatter plot showing the
relationship between
internal training load and
external training load

1200

1201

1202

1203

1400

1500

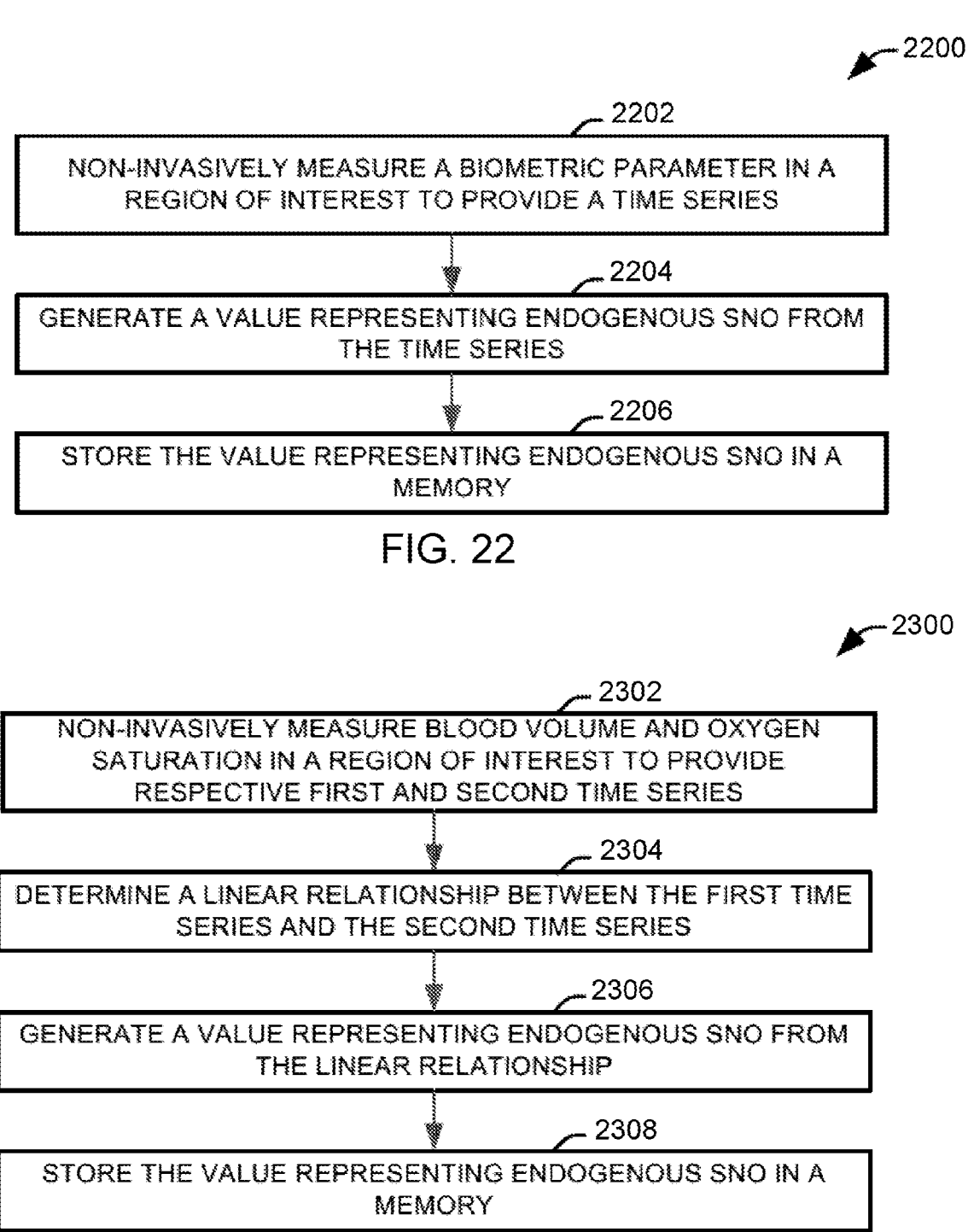

2200

2202
NON-INVASIVELY MEASURE A BIOMETRIC PARAMETER IN A REGION OF INTEREST TO PROVIDE A TIME SERIES

2204
GENERATE A VALUE REPRESENTING ENDOGENOUS SNO FROM THE TIME SERIES

2206
STORE THE VALUE REPRESENTING ENDOGENOUS SNO IN A MEMORY

2302
NON-INVASIVELY MEASURE BLOOD VOLUME AND OXYGEN SATURATION IN A REGION OF INTEREST TO PROVIDE RESPECTIVE FIRST AND SECOND TIME SERIES

2304
DETERMINE A LINEAR RELATIONSHIP BETWEEN THE FIRST TIME SERIES AND THE SECOND TIME SERIES

2306
GENERATE A VALUE REPRESENTING ENDOGENOUS SNO FROM THE LINEAR RELATIONSHIP

2308
STORE THE VALUE REPRESENTING ENDOGENOUS SNO IN A MEMORY

FIG. 23

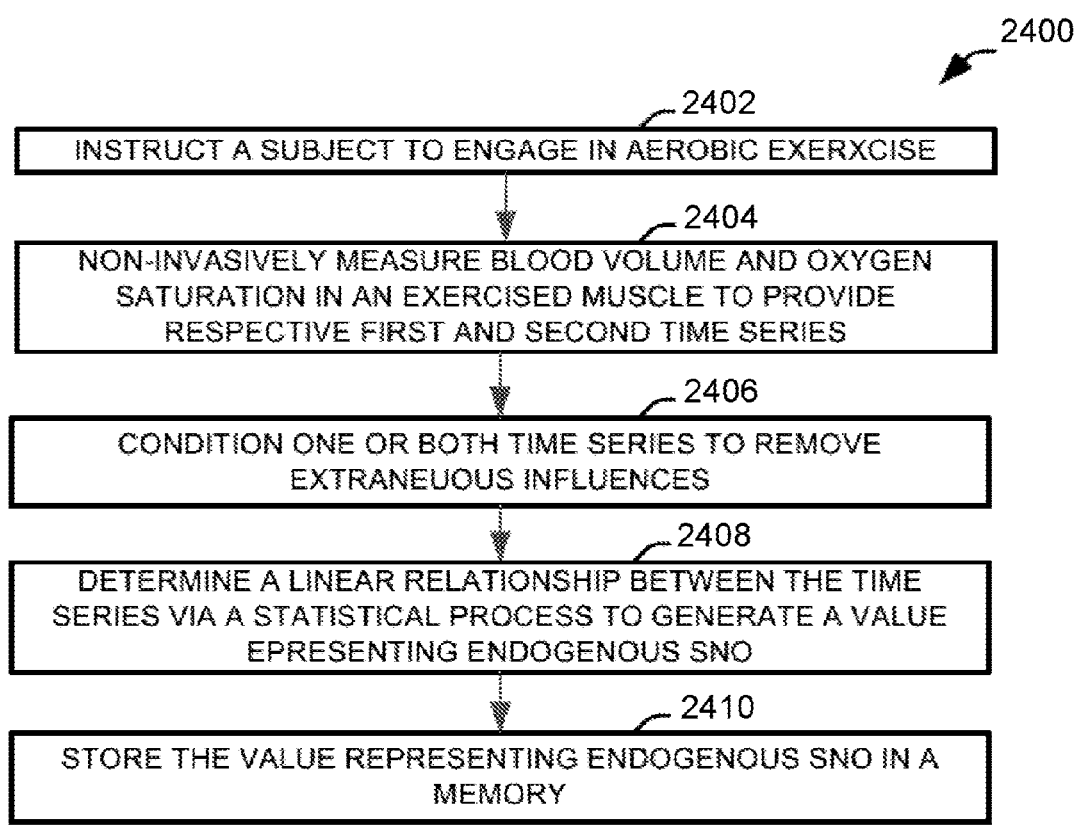

2400

2402
INSTRUCT A SUBJECT TO ENGAGE IN AEROBIC EXERXCISE

2404
NON-INVASIVELY MEASURE BLOOD VOLUME AND OXYGEN SATURATION IN AN EXERCISED MUSCLE TO PROVIDE RESPECTIVE FIRST AND SECOND TIME SERIES

2406
CONDITION ONE OR BOTH TIME SERIES TO REMOVE EXTRANEUOUS INFLUENCES

2408
DETERMINE A LINEAR RELATIONSHIP BETWEEN THE TIME SERIES VIA A STATISTICAL PROCESS TO GENERATE A VALUE EPRESENTING ENDOGENOUS SNO

2410
STORE THE VALUE REPRESENTING ENDOGENOUS SNO IN A MEMORY

FIG. 24

| NFL / Soccer Metric | Use Case(s) |
|---|---|
| Max-(NO) Power | • Improving player's maximal speed / power<br>• Cornerback, wide receiver, running back |
| Max-(NO) Endurance | • Improving player's maximal endurance<br>• Mid-fielder, attack (soccer) |
| (NO)-Recovery | • Accelerate in-game recovery (all sports / positions) |
| (NO)-Regeneration | • Quicker return to play from injury<br>• Reduce injury risk |

| Laboratory results | NOHb measurements | | | | | | | | |
| | SNO-Hb | | | FeNOHb | | | SNO-Hb/Total NOHb | | |
| | n | Corr | p-value | n | Corr | p-value | n | Corr | p-value |
|---|---|---|---|---|---|---|---|---|---|
| Albumin (g/dL) | 33 | 0.11 | 0.5285 | 33 | -0.09 | 0.6178 | 32 | 0.02 | 0.9131 |
| Arterial oxygen tension (pO2) (mmHg) | 33 | -0.01 | 0.9728 | 33 | -0.05 | 0.8006 | 32 | 0.02 | 0.893 |
| Blood urea nitrogen (BUN) (mg/dL) | 33 | -0.03 | 0.8614 | 33 | 0.11 | 0.5402 | 32 | -0.12 | 0.5256 |
| Creatinine (mg/dL) | 33 | -0.13 | 0.4815 | 33 | 0.06 | 0.7501 | 32 | -0.17 | 0.3574 |
| eGFR (ML/MIN/1.73 | 32 | -0.1 | 0.5718 | 32 | -0.11 | 0.5323 | 31 | 0.06 | 0.7316 |
| Glycosylated hemoglobin (HbA1c) (%) | 27 | -0.38 | 0.0516 | 27 | 0.12 | 0.5618 | 26 | -0.28 | 0.1672 |
| Nitrate (μmol/L) | 33 | -0.28 | 0.1123 | 33 | -0.26 | 0.1505 | 32 | 0.03 | 0.8762 |
| Nitrite (μmol/L) | 33 | -0.41 | 0.0191 | 33 | 0.1 | 0.5904 | 32 | -0.36 | 0.0403 |

FIG. 33

| NIRS readings Body location (anatomical location) | NOHb measurements | | | | | | | | |
| | SNO-Hb | | | FeNOHb | | | SNO-Hb/Total NOHb | | |
| | n | Corr | p-value | n | Corr | p-value | n | Corr | p-value |
|---|---|---|---|---|---|---|---|---|---|
| Calf | 23 | -0.32 | 0.1385 | 23 | -0.01 | 0.9717 | 22 | -0.32 | 0.1445 |
| Foot (ankle cuff) | 23 | -0.43 | 0.0421 | 23 | 0.13 | 0.5599 | 22 | -0.54 | 0.0095 |
| Foot (thigh cuff) | 23 | -0.22 | 0.3024 | 23 | 0.01 | 0.9586 | 22 | -0.36 | 0.103 |

FIG. 34

SPECTROMETRY SYSTEMS AND METHODS

CROSS-REFERENCE TO RELATED APPLICATIONS

This application is a U.S. National Stage Application of International Application No. PCT/US23/86145 filed Dec. 28, 2023, which claims the benefit and priority to U.S. Provisional Patent Application No. 63/477,989 filed Dec. 30, 2022, which are incorporated by reference in their entireties.

BACKGROUND

Spectrometry is based on using single or multiple light sources that produce energy of various wavelengths to radiate biological tissue(s). One or more sensors are then strategically placed to detect and measure the energy that exits the sample at distinct locations. The dispersed localization of sources and receivers allows for techniques such as triangulation and time resolution to distinguish signals from locations within the multidimensional tissue sample.

There are many ways in which the source(s) and sensor(s) can be arranged and operated such that one can make many measurements. Each of the measures mentioned above corresponds to the energy contained within a predefined spectral bandwidth of exiting energy. The resulting energy spectrum that is created can be analyzed in many ways to derive the measured sample's physical or chemical characteristics.

SUMMARY OF THE DISCLOSURE

Devices and methods for the non-invasive in vivo quantitative measurement of biomarkers, chemicals, and chromophores in differentiated biological tissue layers and associated blood supply are described herein. More specifically, this disclosure describes a new and more effective method of deriving the desired parameter values for biomarkers, chemicals, and chromophore concentrations from spectrophotometric measurements.

Systems and methods described herein may employ an optical methodology for non-invasively measuring biomarker levels, chemical concentrations, and chromophore concentrations in distinct biological tissue layers. Additionally, the optical methodologies to be taught herein allow for the measurement of biomarkers, chemicals, and chromophores, including but not limited to, oxygenated hemoglobin, deoxygenated hemoglobin, methemoglobin, carboxyhemoglobin, muscle oxygenation, muscle oxygen consumption, nitric oxide, s-nitrosothiols, water, glycogen, and internal training load.

Some example embodiments may include a system comprising at least one light source configured to illuminate a region of interest of a subject, at least one light sensor configured to non-invasively measure reflected light within the region of interest of the subject, at least one processor in communication with the sensor, and at least one non-transitory computer readable medium storing machine-readable instructions. When executed by the at least one processor, the instructions may cause the at least one processor to perform processing comprising receiving at least one measured value of light from the at least one light sensor, processing the at least one measured value and at least a portion of a stochastic model, thereby determining an irradiance distribution for the region of interest of the subject, calculating, from the irradiance distribution, at least one characteristic attenuation coefficient for at least one wavelength of the light, and based on the at least one characteristic attenuation coefficient and the at least one measured value of light, determining at least one physical characteristic of the region of interest of the subject.

Some example embodiments may include a system comprising a plurality of light sources configured to illuminate a region of interest of a subject, the respective light sources of the plurality of light sources being configured to emit light at respectively different wavelengths, at least one light sensor configured to non-invasively measure reflected light within the region of interest of the subject, at least one processor in communication with the sensor, and at least one non-transitory computer readable medium storing machine-readable instructions. When executed by the at least one processor, the instructions may cause the at least one processor to perform processing comprising receiving a plurality of measured values of light at the respectively different wavelengths from the at least one light sensor and determining, from the plurality of measured values of light, at least one thickness or depth of at least one tissue layer within the region of interest of the subject.

Some example embodiments may include a method comprising illuminating, by at least one light source, a region of interest of a subject; detecting, by at least one light sensor, reflected light from the region of interest of the subject; receiving, by at least one processor, at least one measured value of light from the at least one light sensor; determining an irradiance distribution for the region of interest of the subject using the at least one measured value and a stochastic model as inputs: calculating, by the at least one processor, from the irradiance distribution, at least one characteristic attenuation coefficient for at least one wavelength of the light; and based on the at least one characteristic attenuation coefficient and the at least one measured value of light, determining, by the at least one processor, at least one physical characteristic of the region of interest of the subject.

Some example embodiments may include a method comprising illuminating, by a plurality of light sources, a region of interest of a subject, the respective light sources of the plurality of light sources emitting light at respectively different wavelengths; detecting, by at least one light sensor, light within the region of interest of the subject; receiving, by at least one processor, a plurality of measured values of light at the respectively different wavelengths from the at least one light sensor; and determining, by the at least one processor, from the plurality of measured values of light, at least one thickness or depth of at least one tissue layer within the region of interest of the subject.

In at least some of the example embodiments, the processing and/or method may further include determining, based on the at least one measured value of light and at least one thickness or depth of at least one tissue layer, at least one physical characteristic of the region of interest of the subject. In at least some of the example embodiments, the determination may include applying the plurality of measured values of light to at least one scattering phase function associated with at least one layer type within the region of interest of the subject.

In at least some of the example embodiments, the at least one physical characteristic may include one or more of a water measurement, an internal training load, an oxygenated hemoglobin measurement, a deoxygenated hemoglobin measurement, a total hemoglobin measurement, a blood volume measurement, a muscle oxygenation, a muscle oxygen consumption, an active nitric oxide measurement, an active s-nitrosothiols measurement, an adipose thickness, and a melanin content.

In at least some of the example embodiments, the at least one physical characteristic may include a combination of a pulse oximetry and nitric oxide.

In at least some of the example embodiments, the at least one measured value of light may include a time series of measurements and the at least one physical characteristic includes a time series of characteristics. The processing and/or the method may further comprise generating a value representing an endogenous S-nitrosothiol content of tissue within the region of interest from the time series of characteristics and storing the value representing the endogenous S-nitrosothiol content of tissue within the region of interest in the non-transitory computer readable medium.

In at least some of the example embodiments, the time series of characteristics may include a time series of oxygen saturation measurements and a time series of blood volume measurements. In at least some of the example embodiments, the generating of the value may include determining a linearity of relationship between the time series of blood volume measurements and the time series of oxygen saturation measurements and provides a set of parameters, and generating the value representing the endogenous S-nitrosothiol content of tissue within the region of interest from the set of parameters. In at least some of the example embodiments, the generating of the value may include using a linear regression model to provide a best-fit line defined by the set of parameters, the set of parameters including a slope of the best-fit line, and generating the value representing the endogenous S-nitrosothiol content of tissue within the region of interest from the slope of the best-fit line.

In at least some of the example embodiments, the determination of at least one physical characteristic may be performed during one of a period of exercise by the subject and a time period immediately after the period of exercise by the subject.

In at least some of the example embodiments, the processing and/or the method may further include displaying, by at least one display device in communication with the at least one processor, at least one indication of the at least one physical characteristic. In at least some of the example embodiments, the at least one indication may include guidance related to an internal training load of the subject, for example guidance directed towards decreasing a risk of injury. In at least some of the example embodiments, the at least one indication may include information related to a muscle oxygen consumption of the subject, for example information including a VO2 indication.

In at least some of the example embodiments, the stochastic model may include a three-dimensional model with six degrees of freedom. In at least some of the example embodiments, the six degrees of freedom may include location coordinates and direction cosines.

BRIEF DESCRIPTION OF DRAWINGS

FIG. 1 is a wearable optical device according to some embodiments of the disclosure.

FIG. 22 illustrates one example of a method for generating a value representing an endogenous S-nitrosothiol content of tissue within a region of interest of a subject according to some embodiments of the disclosure.

FIG. 23 illustrates another example of a method for generating a value representing an endogenous S-nitrosothiol content of tissue within a region of interest of a subject according to some embodiments of the disclosure.

FIG. 24 illustrates a further method for generating a value representing an endogenous S-nitrosothiol content of tissue within a region of interest of a subject according to some embodiments of the disclosure.

FIG. 33 depicts correlations between NOHb measurements and clinical chemistry results according to some embodiments of the disclosure.

FIG. 34 depicts correlations between NOHb measurements and NIRS half-time to hyperemia according to some embodiments of the disclosure.

DETAILED DESCRIPTION OF SEVERAL EMBODIMENTS

Figure 2:
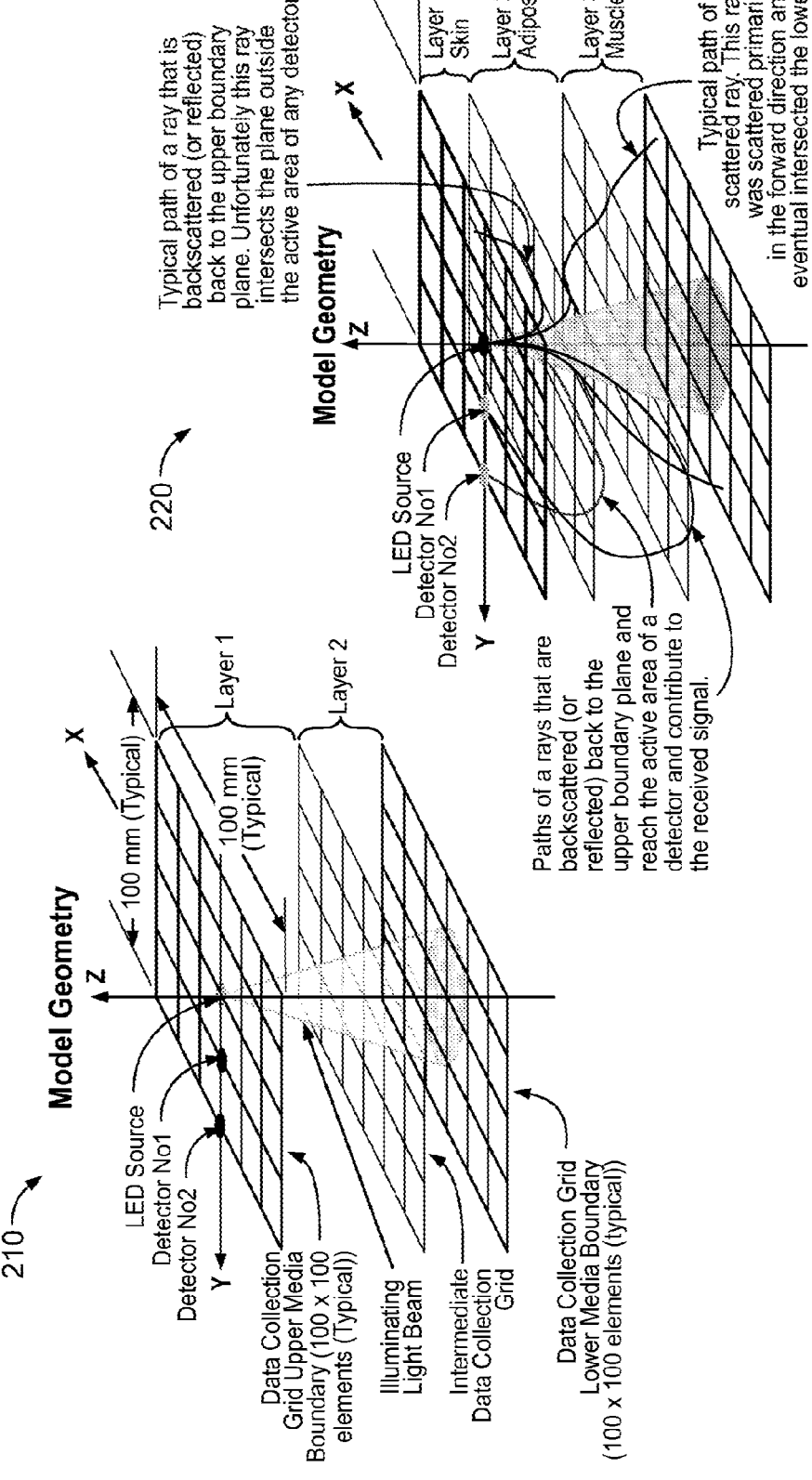
FIG. 2 is a set of illustrations of the modeled geometry for light according to some embodiments of the disclosure.

In the following description, for purposes of explanation and teaching, numerous specific details are set forth in order to provide an understanding of one or more example embodiments. It may be evident, however, to one skilled in the art that other embodiments of the disclosed systems and methods may be practiced without some or all of these specific details.

As used herein, the term "includes" means includes but not limited to, the term "including" means including but not limited to. The term "based on" means based at least in part on. Additionally, where the disclosure or claims recite "a", "an", "a first", or "another" element, or an equivalent thereof, it should be interpreted to include one or more than one such element, neither requiring nor excluding two or more such elements.

As used herein, an "amount" or "level" of a biological substance can represent any of a volume, mass, degree of saturation, or concentration of the biological substance.

As used herein, a "physiological parameter" or "biological parameter" is a continuous, categorical, or ordinal value that characterizes a physical state of a subject.

As used herein, a "biomarker" or "biometric parameter" is a measured parameter that is indicative of the health, fitness, or physical performance of a subject.

As used herein, a "subject" is an organism belonging to the Mammalia class.

As used herein, a "predictive model" is a mathematical model that either predicts a future state of a parameter or estimates a current state of a parameter that cannot be directly measured.

As used herein, a "biometric parameter" is a measured parameter that is indicative of the health or fitness of a subject.

As used herein, a measurement is performed "non-invasively" if it is not necessary to remove blood or tissue from a subject to perform the measurement.

As used herein, a "time series" is a series of measurements on a relative time scale.

The measurements need not be contiguous or on a constant interval.

As used herein, a "providing therapy to a subject" can include administering a therapeutic, applying mechanical force or electrical energy to the subject, or instructing a subject to perform a specific movement or task believed to provide a therapeutic benefit to the subject.

As used herein, "PNO", or personal nitric oxide, is an individual's level of the bioactive form of NO in blood that is derived from red blood cells and identified with S-nitrosothiol in hemoglobin, and it is appreciated that SNO in RBCs is in equilibrium with other SNOs, and that PNO may form from different sources of NO (and related NOx) and that S-nitrosothiol release from RBCs may occur in different ways to generate NO and S-nitrosothiols in tissues, and that PNO therefore represents NO bioactivity, including any bioactive form of NO derived from RBCs or otherwise formed in order to oxygenate tissues. It should be understood that PNO is a relative measure representing a direct correlation between oxygen saturation of hemoglobin and total hemoglobin. By way of example, an individual with a higher level of SNO is able to reoxygenate tissue more quickly than an individual with a lower level of SNO, e.g., muscle recovery during exertion such as exercise routines.

As used herein, "UO2" is the amount of oxygen used by the tissue within a region of interest as measured using a nitric oxide based calculation. The calculation is derived as a product of the PNO metric and an amount of oxygen utilized in the tissue.

As used herein. "Max NO power" is a nitric oxide based measure reflecting an individual's maximal rate of energy utilization that relates directly to true measurements of the rate of energy utilization in Watts and is derived from the maximum value of the PNO metric and the maximum energy utilization by the muscle tissue during exercise, and "Max NO endurance" is a nitric oxide based measure reflecting an individual's maximal rate of energy supply that relates directly to increases in critical power, a gold standard measurement of endurance performance, that is derived from a maximum rate of change of the PNO metric generated in a rest period after exercise.

As used herein, a calculation or determination is made in "real time" when it is available to the user within one minute of a corresponding measurement. In one implementation, real time calculations are performed within ten seconds of the measurement.

Spectrometry has become a well-established and accepted approach to measuring many biological parameters in vivo and in real-time non-invasively. In this context, spectrometry involves using one or more sources that project electromagnetic energy of multiple wavelengths toward tissue for which measurements are desired and one or more detectors to detect and measure the energy that exits the tissues. The energy source is generally located externally to the body and directed toward the tissue, or body part, of interest. The energy propagates through the skin and into subcutaneous tissues, including adipose and skeletal muscle tissue. As the energy propagates through the body, it is absorbed and scattered, as it would commonly be in a turbid medium, and a fully diffuse energy field is created. Commonly, a portion of the scattered energy reaches a boundary between the tissue and the surrounding environment and propagates transcutaneously out of the tissue. This energy can be detected and measured by placing appropriate sensors on the appropriate tissue boundary. The detected energy forms a spectroscopic signal that carries an imprint of the material through which the energy has passed. An important part of any spectroscopic system is how the spectroscopic signal is processed, how the imprint is extracted, and how the imprint is interpreted.

By creatively selecting the wavelengths, which can be outside or within the visible light spectrum, that are used, the characteristics and placement of the source(s) and receiver(s), and the data processing techniques that are applied, a wide range of material and chemical properties and concentrations can be detected and quantified. The quantifiable biomarker levels, chemical concentrations, chromophore concentrations, and tissue characteristics include but are not limited to oxygenated hemoglobin, deoxygenated hemoglobin, methemoglobin, carboxyhemoglobin, muscle oxygenation, muscle oxygen consumption, nitric oxide, nitric oxide activity in the blood, s-nitrosothiols, water, glycogen, adipose tissue thickness, melanin, and internal training load.

The embodiments discussed herein include a method of spectrophotometric measurement for the in vivo quantification of biomarkers, chemicals, and chromophores in differentiated tissue layers and said tissue layer's associated blood supply. The disclosed embodiments can rely upon one or more body-worn sensors, such as the NNOXX wearable, radiate a desired tissue volume, and then detect and measure the energy that exits the tissue sample at distinct locations. The dispersed localization of sources and receivers allows for techniques such as triangulation and time resolution to distinguish signals from specific locations within the multidimensional tissue sample. There are many ways in which the source(s) and sensor(s) can be arranged and operated such that one can make many measurements. Each of the measures mentioned above corresponds to the energy contained within a predefined spectral bandwidth of exiting energy. The resulting energy spectrum that is created can be analyzed in many ways to derive the measured sample's physical or chemical characteristics. Said measured sample provides quantitative measurements of biomarkers including but not limited to oxygenated hemoglobin, deoxygenated hemoglobin, methemoglobin, carboxyhemoglobin, muscle oxygenation, muscle oxygen consumption, nitric oxide, nitric oxide activity in the blood, s-nitrosothiols, water, glycogen, adipose tissue thickness, melanin, and internal training load.

An integrated hardware and/or software system then receives information from the body-worn sensors and automatically provides biofeedback such as biomarker, chemical, and chromophore levels in a specified tissue layer or vascular network. The disclosed embodiments can process one or more algorithms that take both in-vivo sensor measurements and stochastic model data as inputs, thereby providing powerful and accurate measurements of one or more physical characteristics of a subject. For example, assume an individual is exercising as a means of enhancing cardiovascular function. Such an individual may use the NNOXX wearable, or another spectrophotometric device, to measure specified biomarker measurements such as active nitric oxide levels in the skeletal muscle tissue to determine the most effective exercise intensity to achieve their goals. Alternatively, a physician may use the spectrophotometric device discussed herein to non-invasively measure a patient's blood biomarkers including, but not limited to, nitric oxide, iron, cholesterol, blood oxygenation, and muscle oxygenation.

Figure 5:
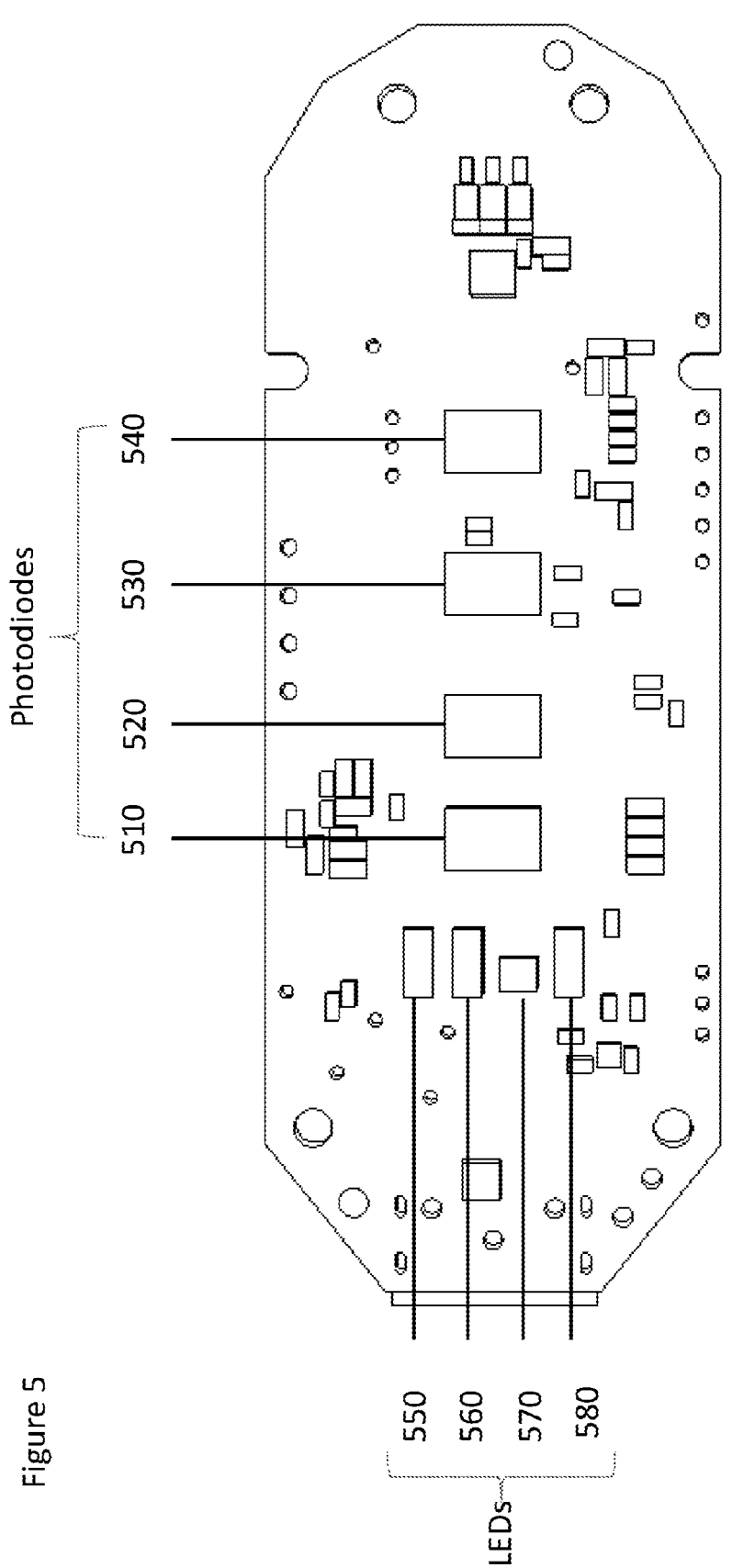
FIG. 5 is an example set of optical hardware LEDs and photodiodes according to some embodiments of the disclosure.
Figure 6:
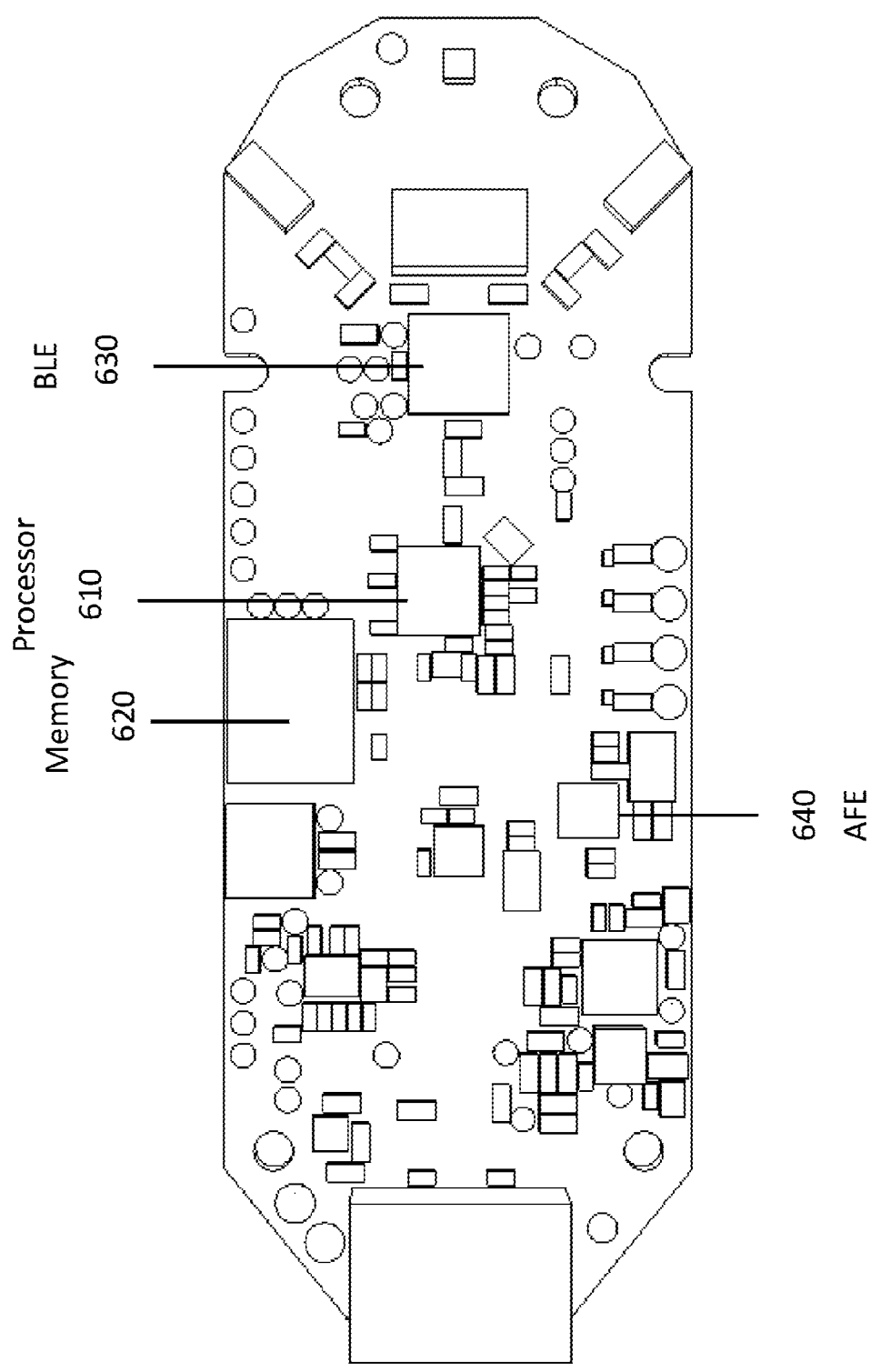
FIG. 6 is an example of optical hardware used to control and capture light and process data according to some embodiments of the disclosure.

In the systems and methods described herein, the following processing can be performed by one or more hardware and/or software systems such as those described herein with respect to FIGS. 5 6, 12, and/or 13 for example, each of which is described in detail below.

Consider a collimated beam of light passing through a bounded volume of a turbid medium. Turbid media are transparent or semi-transparent materials that absorb and scatter any light that passes through them. Collimated beams may be used because a superposition of collimated beams of varying intensity can mathematically describe the radiant intensity distribution of any light source. As the beam of light passes through the turbid medium, the energy in the beam is reduced by the processes of absorption and scattering in accordance with Equation (1)

$$I(z) = I_o \exp\left(-(\mu_a + \mu_s)z\right) \tag{1}$$

$I_o$, in equation (1), represents the initial intensity of the beam as it enters the turbid medium. z represents the distance traveled by the beam through the turbid medium. I(z) is the intensity of the beam at distance z. $\mu_a$ is equal to the absorption coefficient associated with the turbid medium which describes that geometric rate at which energy is absorbed from the beam. Finally, $\mu_s$ is equal to the scattering coefficient associated with the turbid medium which describes the geometric rate at which energy is scattered from the beam.

Equation (1) is the familiar Beer's Law which states that the intensity of a beam of light is reduced at an exponential geometric rate by the combined effects of absorption and scattering. The sum of the absorption coefficient, $\mu_a$, and the scattering coefficient, $\mu_s$, is termed the attenuation coefficient, c, as shown in Equation (2). The processes of absorption and scattering are independent, both functionally and mathematically.

$$\mu_a + \mu_s = c \qquad (2)$$

Now consider the collimated beam of light as a bundle of parallel rays. Each ray represents a small portion of the beam's energy, and a superposition of many beams of varying intensity represents the light source. Consider absorption as a continuous process along the path of the ray per Beer's Law. Furthermore, scattering is a series of discrete events occurring at random locations along the ray's path. The distance between scattering events is determined randomly in accordance with Equation (3).

$$d = -\ln(q)/\mu_s \qquad (3)$$

The variable d in equation (3) represents the distance along the ray between sequential scatter events. The variable q in equation (3) is equal to a random number that follows a normal distribution between 0 and 1. The variable $\mu_s$ in equation (3) is equal to the scatter coefficient that is characteristic of the medium in which the scatter event occurs.

The Scatter Phase Function, also known as the Volume Scatter Function, is the final parameter that must be defined. In the Scatter Phase Function, $p(\theta)$, the variable p is the probability density function that is used to predict the polar angle, $0°<\theta<180°$, through which the direction of the ray will be changed as the result of a scatter event. In three dimensional models, such as described herein, an azimuthal angle, which is uniformly distributed between $0°<\phi<360°$, must also be stochastically chosen.

If one stochastically picks an individual ray from an individual beam through the turbid medium, per the radiant distribution of the light source, one can stochastically trace the ray through the turbid medium. One can stochastically trace the ray through the turbid medium because picking the ray determines its initial direction, and all rays start with the same energy. Furthermore, by doing this for many individual rays, one can develop the probable light field.

The geometry for the model is shown in FIG. 2. The model 210 is three-dimensional with six degrees of freedom (x,y,x,a,b,c) where x, y, and z are location coordinates and a, b, g are direction cosines. The media volume is a rectangular volume defined by an upper boundary plane and a lower boundary plane, both of which have defined dimensions on the order of 100 mm×100 mm. The model 210 is stratified by the definition of horizontal intermediate planes that divide the rectangular volume into parallel horizontal slabs or layers. FIG. 2 shows the media volume to be divided into two layers by a single intermediate plane, but any number of intermediate planes and layers can be defined. It is common to define three layers: a top layer representing skin, an intermediate layer representing adipose, and a lower layer representing muscle. The optical characteristics and physical thickness of each layer can be defined independently. Multiple light sources (commonly LEDs) and multiple optical detectors (commonly photodiodes) can be placed anywhere on the Upper Media Boundary layer.

Conceptual ray paths are shown in FIG. 2. The ray paths 220 that are of interest are the ones that end within the active area of a detector. All others are considered lost due to scattering. Typical scattering coefficient values for skin, adipose, and muscle are on the order of 10/mm to 50/mm. This means that the characteristic distance between scatter events is on the order of 0.1 mm to 0.02 mm. For a detector that is positioned 25 mm from the source, the typical path distance for a ray that reaches this detector will be on the order of 100 m to 150 mm. This means that a typical ray that reaches the detector will have experienced a scatter event on the order of 1000 to 7500 times. This metric is a good indicator of how diffuse the light field within the turbid medium is.

Figure 3:
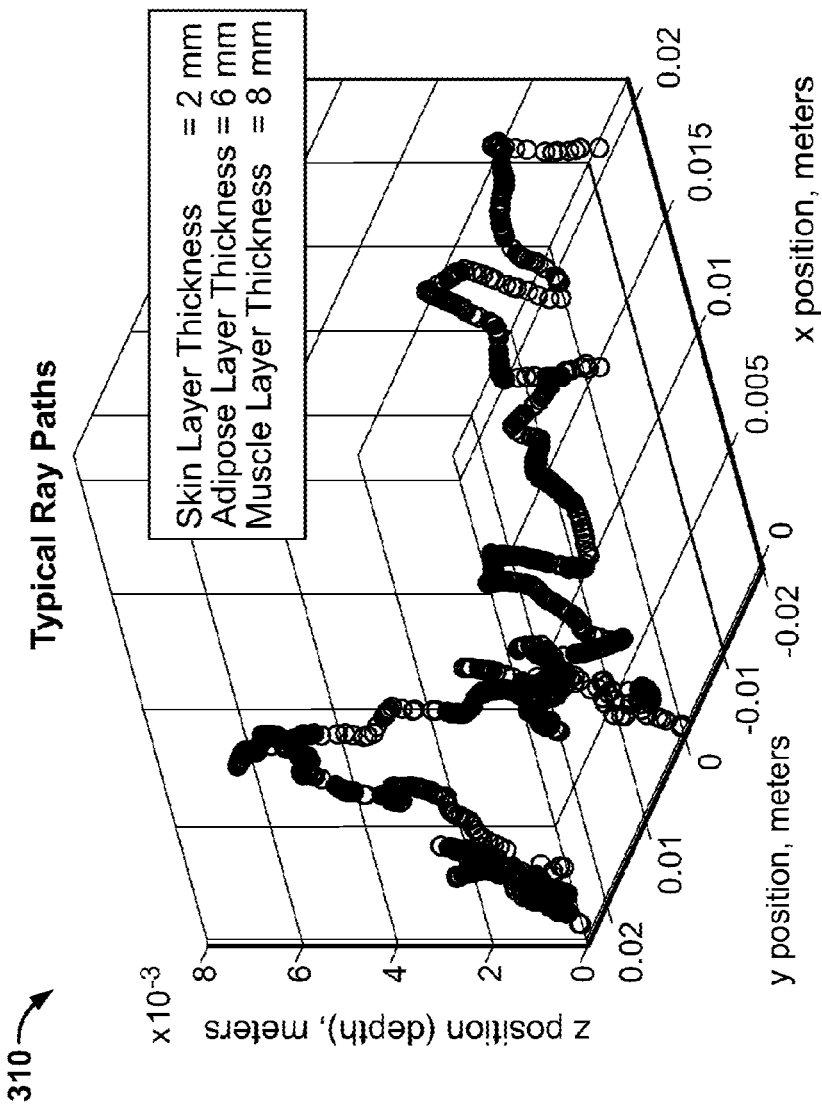
FIG. 3 is a graph illustrating an example ray path for photons according to some embodiments of the disclosure.

FIG. 3 presents two calculated ray paths 310. Both rays originated at point (0,0,0) and ended in the upper boundary plane 25 mm distant from the origin. These paths 310 show how torturously convoluted typical ray paths are.

The primary product produced by the stochastic model is the upwelling irradiance distribution incident on the upper media boundary. This irradiance distribution is calculated by tracing on the order of 1.0e+09 rays. Each ray is traced until it has experienced 20,000 scatter events or until it has intersected one of the six media boundaries, upper and lower horizontal boundaries, plus four vertical boundaries. If the ray intersects the upper horizontal boundary, then the coordinates of its intersection are calculated, and the boundary element in which it "landed" is identified. Then various parameters associated with the ray are stored in files associated with this boundary element. Three of the many parameters that are calculated and stored for each ray include 1) the residual, post absorption, 'energy' of the ray, 2) the maximum depth to which the ray penetrated the medium, and 3) the geometric distance the ray traveled on its journey from the source to the upper boundary plane. After all rays have been traced, it is possible to sum all the ray 'energy' values for each boundary element, giving a distribution of energy/unit area related to irradiance.

Once the irradiance distribution on the upper boundary plane is calculated, it is possible to calculate the relative signal that would be received by any size detector placed at any location on the upper boundary plane. This is termed a relative signal because the units are (residual ray energy)/mm. Each ray is assigned an energy value of 1.0 when it is selected at the source; then, this value is reduced by absorption as the ray passes through the various layers of the turbid medium. The irradiance value that is calculated for each element of the upper boundary plane is the sum of residual, or non-absorbed, energy values for the rays that intersect the upper boundary plane within the limits of that element. This makes it possible to calculate scattering losses as follows.

$$I_{detected} = N * F * I_o * \exp\left(-\sum \mu_{a,i} * L_i\right) \qquad (4)$$

The variable $I_{detected}$ in equation (4) equals the "energy" incident on the active area of one of the optical detectors. The variable N in equation (4) is equal to the total number of rays traced. The variable $I_O$ in equation (4) equals the initial energy assigned to each ray (1.0). The variable F in equation (4) is equal to the loss due to scattering. The variable $\mu_{a,i}$ in equation (4) is equal to the absorption coefficient for the layer $L_i$. The variable $L_i$ in equation (4) is equal to the path length, or distance, traveled by the ray through layer I. Finally, the variable $\exp(-\Sigma\mu_{a,i}*L_i)$ in equation (4) is equal to the accumulate absorption losses. By setting all $\mu_{a,i}$ to 0 we get equation (5) and since $I_o=1$ we can derive equation (6).

$$I_{detected} = N * F * I_o \qquad (5)$$

$$F = I_{detected}/N \qquad (6)$$

A unique value of F can be calculated for each data collection element in the upper boundary plane. The values of F are dependent on the values chosen for the scattering coefficient, $s_i$, the Scattering Phase Functions that are chosen for each layer, and the thickness of each layer. All these inputs are chosen from the open literature. A key point is that the value of F is independent of absorption. Once a value for F has been calculated the model can be run with non-zero values for the $\mu_{a,i}$'s. A useful process is to set all $\mu_{a,i}$'s to a single value, $\mu_a$. When this is done, the following equation (7) can be written. Additionally, equation (7) can be rewritten as equation (8).

$$I_{detected} = N * F * I_o * \exp(-\mu_a * L) \qquad (7)$$

$$L = \left(-\ln\left(I_{detected}/(N * F * I_o)\right)\right)/\mu_a \qquad (8)$$

L in this case describes a characteristic distance that the rays have traveled from the light source to the upper boundary plane. A value for L can be calculated for each element of the plane. By running the model multiple times specifying a different, unique value for each time a set of values for $(\mu_a, L)$ pairs can be calculated. It is then possible to derive a mathematical relation between a and L and describe L as a function of $\mu_a$, or $L=f(\mu_a)$. Once values for the characteristic attenuation coefficient have been calculated for several wavelengths they can be put to practical use. Consider the equation:

$$\mu_a(\lambda) = 2.3 \sum c_i \varepsilon_i(\lambda) + \sum V_n \mu_n(\lambda) \qquad (12)$$

This equation connects the wavelength dependent characteristic absorption coefficients, $\mu_a(\lambda)$, extinction coefficients, $\varepsilon_i(\lambda)$ to several biological parameters, in this case volume fractions, and concentrations, $c_i$. The application described herein is primarily focused on the time varying optical and biological characteristics of the blood supply. Therefore, parameters that are very small or invariant in time can be set to zero. By so doing, Equation (12) can be rewritten as $$\mu_a(\lambda) = B (S \, \mu_{a,HbO}(\lambda) + (1 - S) \mu_{a,Hb}(\lambda)) + W \, \mu_{a,water}(\lambda) \qquad (13)$$

The variable $m_a(\lambda)$ in equation (13) is the characteristic absorption coefficient measured by the spectrometer. The variable $\mu_{a,HbO}(\lambda)$ in equation (13) represents the absorption coefficient for oxygenated hemoglobin. The variable $\mu_{a,Hb}(\lambda)$ in equation (13) equals the absorption coefficient for deoxygenated hemoglobin. The variables B, S, and W in equation (13) equal the blood volume fraction, oxygen saturation percentage, and water volume fraction respectively. Finally, the variable $\mu_{a,water}(\lambda)$ in equation (13) equals the absorption coefficient for water. Equation (13) contains three variables for which values are unknown, B, S, and W, all of which are wavelength independent.

In a fully equivalent manner Equation (13) can be rewritten as $$\mu(\lambda) = 2.3 * c_{HbO} * \varepsilon_{HbO}(\lambda) + 2.3 * c_{Hb} * \varepsilon_{Hb}(\lambda) + W \, \mu_{a,water}(\lambda) \qquad (14)$$

The variables $c_{HbO}$ and $E_{HbO}$ in equation (14) equal the molar concentration and molar extinction coefficients of oxygenated hemoglobin respectively. The variables $c_{Hb}$ and $\varepsilon_{Hb}$ in equation (14) equal the molar concentration and molar extinction coefficients of deoxygenated hemoglobin respectively. The variables W and $\mu_{a,water}(\lambda)$ in equation (14) equal the water volume fraction and absorption coefficient for water respectively. Equation (14) contains three variables $(\varepsilon_{HbO}(\lambda), \varepsilon_{Hb}(\lambda),$ and $\mu_{a,water}(\lambda))$ for which values are unknown, and three variables $(c_{HbO}, c_{Hb},$ and W) which are unknown, but which are wavelength independent.

FIG. 1 is an image of an embodiment of a wearable optical device 100 that may be used to capture, process, and return non-invasively measured biomarker levels, chemical concentrations, and chromophore concentrations in distinct tissue layers. In some embodiments, the device 100 may include a spectrometer that uses six individual light sources, each with a distinct spectral output. In the model images of FIG. 2, an example embodiment of the optical hardware light emitting diodes (LEDs) and photodiodes used to create an array of source and receivers is illustrated relative to the model geometry. As an example of how the hardware of device 100 may be configured, FIG. 5 shows an example embodiment of optical hardware LEDs 550, 560, 570, 580 and photodiodes 510, 520, 530, 540 that may be used to create an array of sources and receivers. The LEDs in the array may be specified by wavelength and radiance for specified outcomes. The array of photodiodes may be physically placed in a distance from the source for specified outcomes. Note that while four LEDs and four photodiodes are illustrated in this example, it may be understood that any number of LEDs and/or photodiodes may be included (e.g., six LEDs, each with its own distinct spectral output). In addition, FIG. 6 is shows an example embodiment of the optical hardware used to control and capture light, process, and store in memory, before transmitting data wirelessly over Bluetooth. Such hardware may include, but is not limited to, processor 610, memory 620, Bluetooth transceiver 630, and/or analog front end (AFE) 640. Light information may be stored in memory before, during, or after a computation process is applied. Once a desired outcome is achieved, the data may be stored on the device, shown through a connected screen, transmitted in real-time or later via USB. Bluetooth, wireless, or any radio signal.

The LEDs in the array are specified by wavelength and radiance and are physically placed at specific distances from the sources to achieve specific outcomes. By implementing six LEDS, each outputting a different wavelength or band of wavelengths, six independent equations similar to equation (13) or equation (14) can be constructed. These six equations can then be used to calculate values for the independent variables. B, S, and W. or equivalently $c_{HbO}, c_{Hb},$ and W, can then be calculated over time using conventional least-squares techniques.

In one specific example embodiment, the wavelengths of the sources and the locations of the detectors for a device are chosen to optimize the sensitivity of the spectrometer to variations in the concentrations of oxygenated hemoglobin and deoxygenated hemoglobin. In this example, the LED light sources are grouped closely together in a manner that minimizes the separation between them. The peak output wavelengths of the chosen LEDs are 535 nm, 655 nm. 760 nm, 800 nm, 855 nm, and 940 nm. The 800 nm wavelength was chosen because it is close to the isosbestic wavelength for hemoglobin. At this wavelength the received signal will exhibit minimum variation due to changes in oxygenated hemoglobin and deoxygenated hemoglobin concentrations. Also, at this wavelength the received signal will provide a relatively direct indication of total hemoglobin concentration. The 655 nm wavelength and the 760 nm wavelength were chosen to provide two sources whose peak output wavelengths are less than the isosbestic wavelength. Similarly, the 855 nm wavelength and the 940 nm wavelength were chosen to provide two sources whose peak output wavelengths are greater than the isosbestic wavelength. The 535 nm wavelength was chosen to provide a received signal that is exceptionally sensitive to variations in the ratio of the concentration of oxygenated hemoglobin to the concentration of deoxygenated hemoglobin. The 535 nm signal received by the photodiode that is placed closest to the source is dominated by oxygenated/deoxygenation ratio of hemoglobin that is located close to the surface of the radiated tissue and can therefore be used for pulse oximetry. The light that is reflected, or backscattered, by the radiated tissue is received by four light sensitive photodiodes. These photodiodes are placed in a linear array with individual photodiodes placed at distances of 7 mm, 13 mm, 20 mm and 28 mm from the geometric center of the LED group. The signal received by the 7 mm diode is strongly dominated by light that is reflected by tissue that is located close to the radiated surface. Signals that are received by photodiodes that are placed at greater distances from the light source(s) are dominated less strongly by surficial tissue and show characteristics that are increasingly characteristic of deeper tissue (tissue that is located further from the surface) as the source to detector separation increases. By analyzing and comparing the individual signals from the four separate photodiodes it is possible to separately identify optical characteristics that are associated with various tissue layers.

In a similar manner, by properly selecting the optical wavelengths of the sources, specifying locations for the detectors, interpreting the received signals using the computed results of the stochastic model, and building equations similar to equation (13) or equation (14), the spectrometer described herein can be adapted to measure other biomarkers, and tissue properties including, but not limited to, muscle oxygen consumption, muscle oxygen saturation, nitric oxide/s-nitrosothiol, oxygenated hemoglobin, deoxygenated hemoglobin, oxygenated myoglobin, deoxygenated myoglobin, total hemoglobin/blood volume, carboxyhemoglobin, methemoglobin, glycogen concentration, water, potassium, iron, bile, and melanin. For example, embodiments described herein can be used to perform the measurements described in detail below.

The layered structure of the stochastic model enables several unique capabilities, one of them being the ability to empirically estimate the geometric thickness of individual tissue layers. The model supports the definition of any number of individual layers, a typical number for useful analysis being four. The optical characteristics and geometric thickness of each layer can be defined individually to represent, for example, skin, adipose tissue, and muscle. Running the model several times, specifying a different value of, for example, adipose tissue layer thickness each time makes it possible to define adipose tissue layer thickness as a function of optical parameters that can be measured. This connection between adipose tissue layer thickness and measurable optical parameters makes it possible to empirically estimate tissue layer thickness using spectroscopic techniques.

Figure 4:
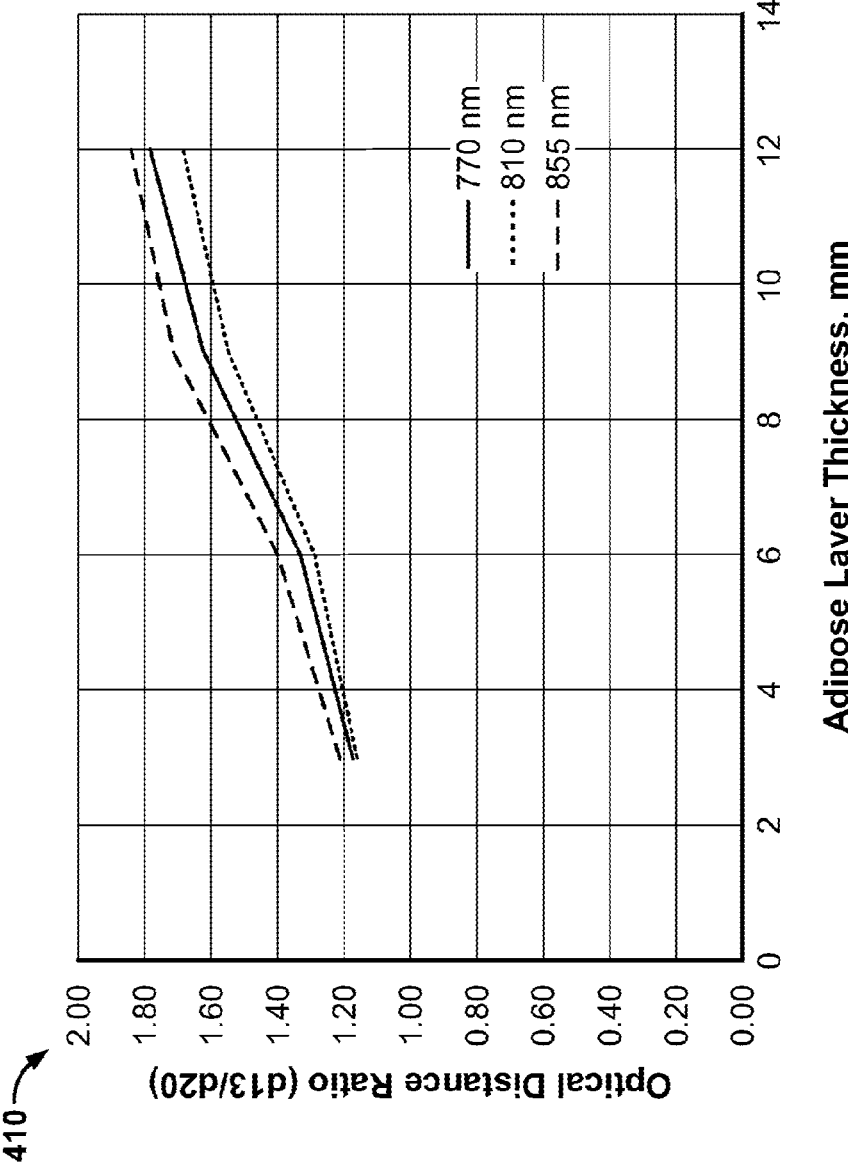
FIG. 4 is a graph illustrating example wavelengths and their optical distance through adipose layer thickness according to some embodiments of the disclosure.

As an example, FIG. 4 shows the thickness of the adipose tissue layer to be a monotonic function of the ratio of two optical parameters, d13 and d20. These optical parameters can be quantified via a combination of stochastic calculations and spectrophotometric measurements. Once the optical parameters are quantified, they can be used to empirically estimate adipose tissue layer thickness via the graphs 410 shown in FIG. 4.

In summary, the advanced data collection device described herein can include six light sources and four independent light sensors. The stochastic light propagation model is fully three dimensional with six degrees of freedom and accommodates a three-dimensional tissue model with spatially variable optical properties. Data processing algorithms used by the device have been developed to take full advantage of the spectral diversity of the light sources and the spatial diversity of the light detectors. Taken together as a whole, this integrated set of capabilities provides the ability to measure the optical properties of individual layers of tissue and thereby map the volumetric distribution and variability of various biological parameters throughout a three-dimensional tissue sample.

Figure 7:
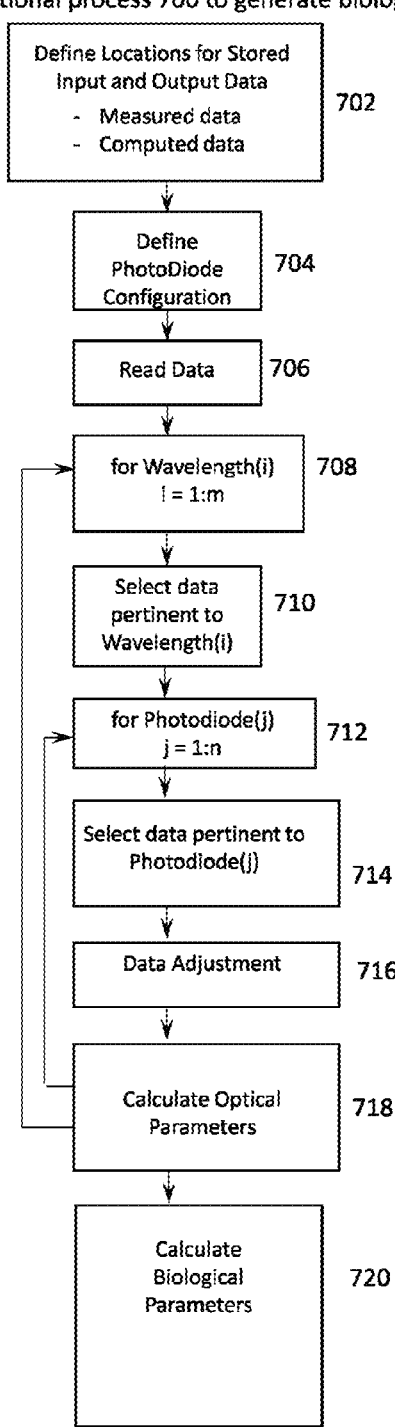
FIG. 7 is a flowchart illustrating a method used to implement a computational process for generating biomarker levels, chemical concentrations, and chromophore concentrations in distinct tissue layers according to some embodiments of the disclosure.

FIG. 7 is a flowchart illustrating a typical method 700 used to implement a computational process for calculating values for various biomarkers, biological properties, chemical concentrations, and/or chromophore concentrations in distinct tissue layers and their associated blood supply, according to some embodiments of the invention. Process 700 can be performed by one or more hardware and/or software systems such as those described herein with respect to FIGS. 5, 6, 12, and/or 13 for example (e.g., the processors and memory systems thereof). Process 700 can effectively utilize data for any number of wavelengths, m, from any number of sensors such as n Photodiodes. By performing a process such as process 700, a device can analyze and/or determine a variety of physical, chemical, and/or biological characteristics of a subject.

At 702, the processor of the device performing process 700 can define the locations, such as paths and filenames, where digital input and output data, including measured data as detected by the one or more photodetectors and computed data determined by the stochastic model is stored. At 704, the processor of the device performing a process such as process 700 can define a configuration of the photodiodes. Such configuration may include the number of photodiodes used, the physical arrangement and geometric location of the photodiodes, and/or the internal configurations of the photodiodes. At 706, the processor of the device performing process 700 can read data collected by the photodiodes, data calculated by the stochastic model, and/or pertinent data from other sources. At 708, the processor of the device performing process 700 can begin processing in a manner that is consistent with the data read at 706. For example, the processor may evaluate the data according to the equations described above. In particular, in some embodiments for which there are data for multiple wavelengths, the processor of the device performing process 700 may enter a loop wherein data are selected and processed for each wavelength in succession. At 710, the processor of the device performing process 700 can select data pertinent to the specific wavelength being processed. For embodiments in which there are data for multiple sensors, such as multiple photo-diodes, the processor of the device performing process 700 may enter a second loop at 712 wherein data are selected and processed for each sensor in succession. At 714, the processor of the device performing process 700 can select data pertinent to the specific sensor being processed. At 716, the processor of the device performing process 700 can perform adjustments, such as averaging, offset correction, and/or orthogonal correction, to the data. At 718, the processor of the device performing process 700 can calculate optical parameters such as absorption coefficients, optical pathlengths, and/or effective geometric pathlengths. At 720, the processor of the device performing process 700 can calculate biological parameters such as Blood Volume Fraction, Water Volume Fraction, and/or Blood Oxygenation percentage (see equations 12-14 above for examples of such calculations).

Figure 8:
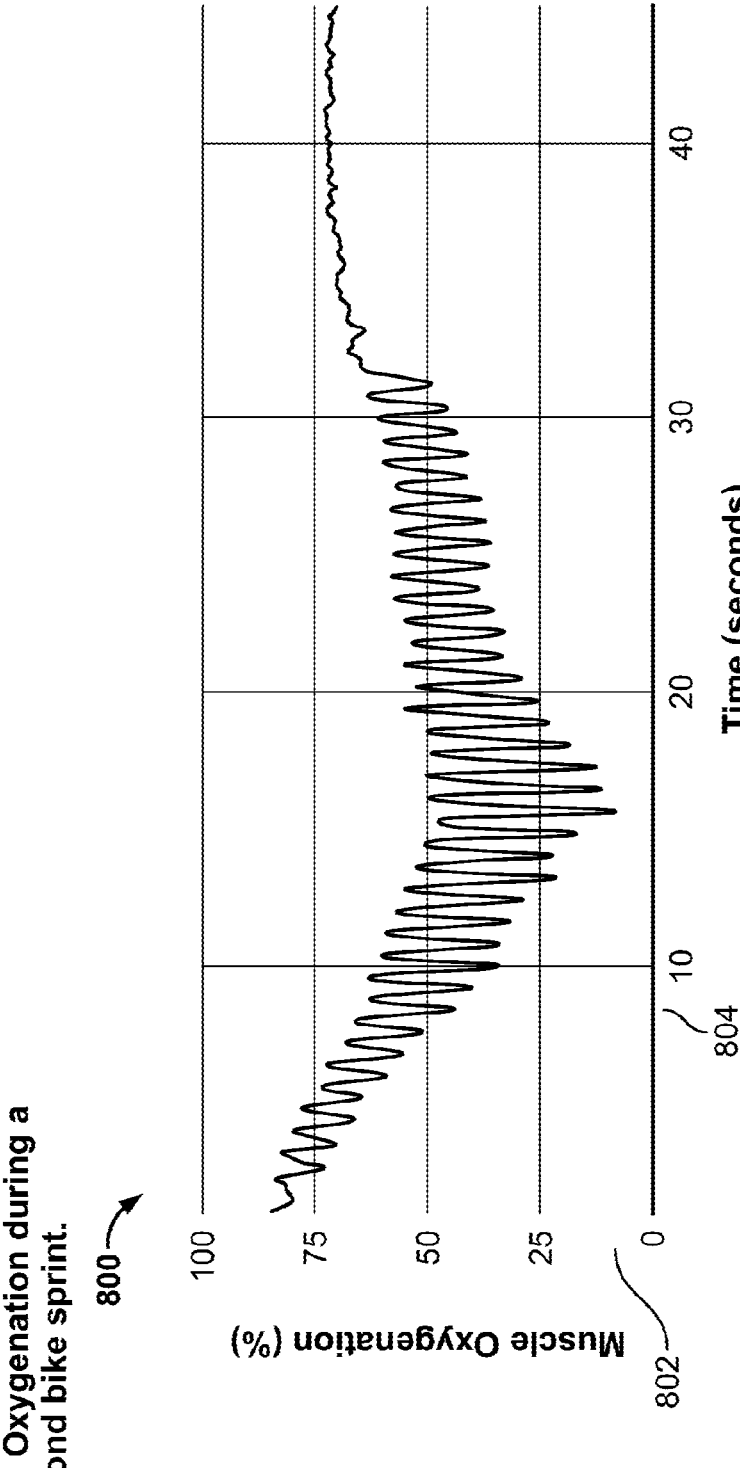
FIG. 8 is a graph illustrating an example of a muscle oxygen saturation (SmO2) measurement for a subject during exercise according to some embodiments of the disclosure.

Biological substances, chemical concentrations, and chromophore levels are not uniformly distributed throughout the human or mammalian body. Thus, the ability to measure biomarker, chemical, and chromophore levels in distinct tissue layers provides advantages over traditional measurement techniques. The spectrophotometric measurement techniques described herein thus allow for a new and more effective method of quantifying biometric parameters. One such biometric parameter is muscle oxygen saturation (SmO2). Muscle oxygen saturation (SmO2) can only be measured by isolating the previously mentioned spectrophotometric measurement to the microvascular capillaries within a muscle tissue. The reason for this is that oxygen saturations vary significantly between different regions of the mammalian circulatory system. For example, the arteries, arterioles, capillaries, venules, and veins all have different oxygen saturations under normal physiological conditions. FIG. 8 illustrates an SmO2 measurement for an individual during exercise using the previously mentioned measurement methodologies. Muscle oxygenation (SmO2) reflects the dynamic balance of oxygen supply and oxygen utilization in exercising muscles. Thus, during periods of muscle contraction SmO2 decreases as oxygen demand supersedes supply. Between muscle contractions SmO2 rises as oxygen supply supersedes demand. By measuring a subject's muscle oxygenation one can gain insights into the primary determinates of exercise performance: oxygen supply and oxygen utilization. The SmO2 data can then be used to design personalized exercise protocols to enhance a subject's health and fitness.

FIG. 8 is a graph 800 illustrating an example embodiment providing a muscle oxygen saturation (SmO2) measurement for a subject during exercise. The vertical axis represents the muscle oxygenation level 802 on a zero to one hundred percent scale, and the horizontal axis represents the duration of exercise 804 in seconds. The muscle oxygenation level at each time point is indicated as a solid black line on the graph.

Other biometric parameters that can be non-invasively measured using the spectrophotometric measurement techniques described herein include, but are not limited to, muscle oxygen consumption, nitric oxide, oxygenated hemoglobin, deoxygenated hemoglobin, oxygenated myoglobin, deoxygenated myoglobin, carboxyhemoglobin, methemoglobin, glycogen concentration, water, potassium, iron, bile, melanin, and adipose tissue thickness.

Figure 9:
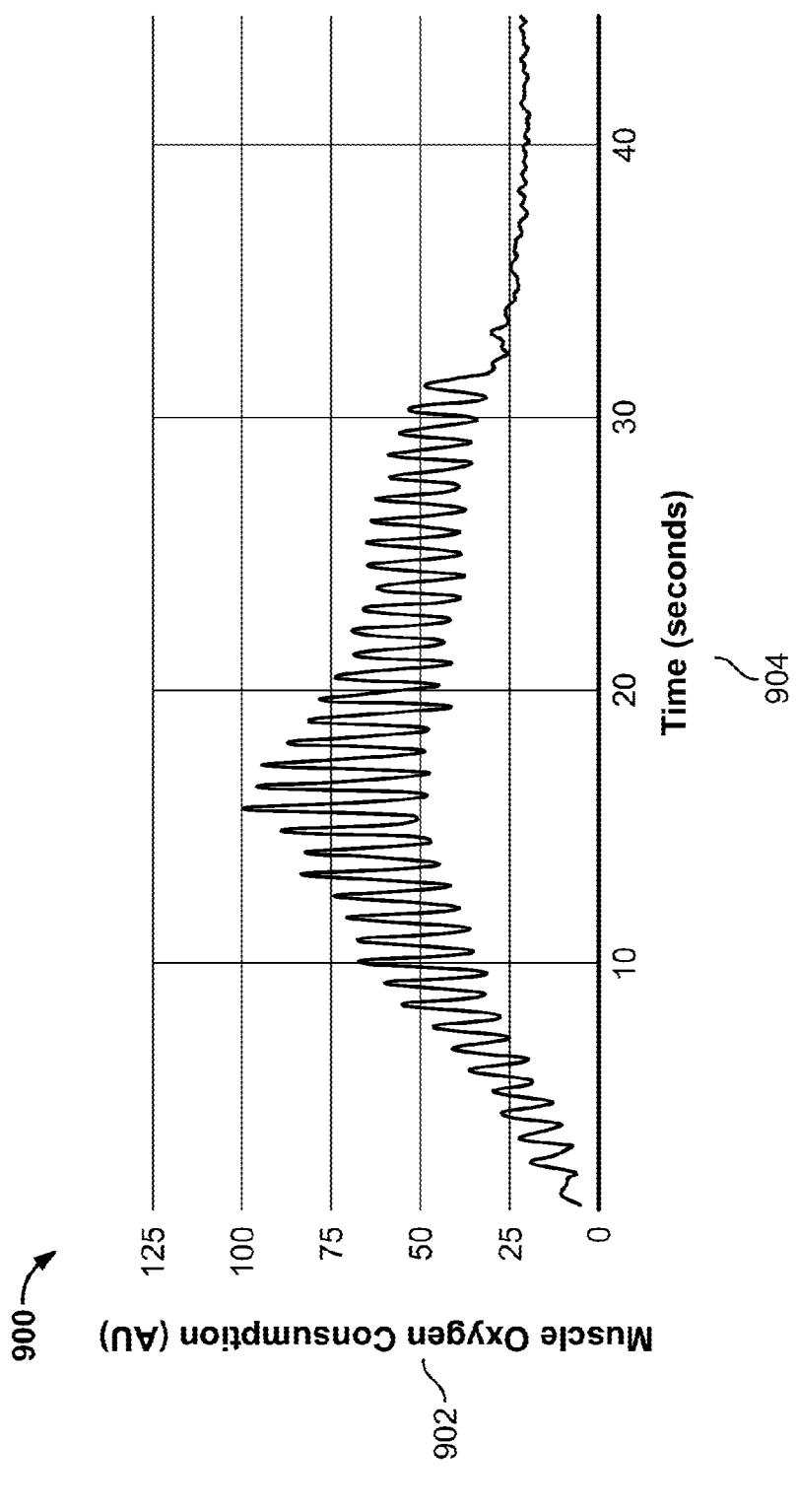
FIG. 9 is a chart illustrating an example of a local muscle oxygen consumption (mVO2) measurement for a subject during exercise according to some embodiments of the disclosure.

FIG. 9 is a chart 900 illustrating a muscle oxygen consumption (mVO2) measurement for an individual during exercise. The vertical axis represents the muscle oxygen consumption level 902, and the horizontal axis represents the duration of exercise 904 in seconds. The muscle oxygen consumption level at each time point is represented by the solid black line on the graph. Prior to exercise muscle oxygen consumption (mVO2) is low and increases during exercise before returning to a baseline level following exercise. Muscle oxygen consumption (mVO2) is strongly correlated with VO2, a gold standard fitness measurement, recorded with a lab-grade metabolic analyzer. Thus, muscle oxygen consumption can be used to quantify an individual's current level of fitness.

Figure 10:
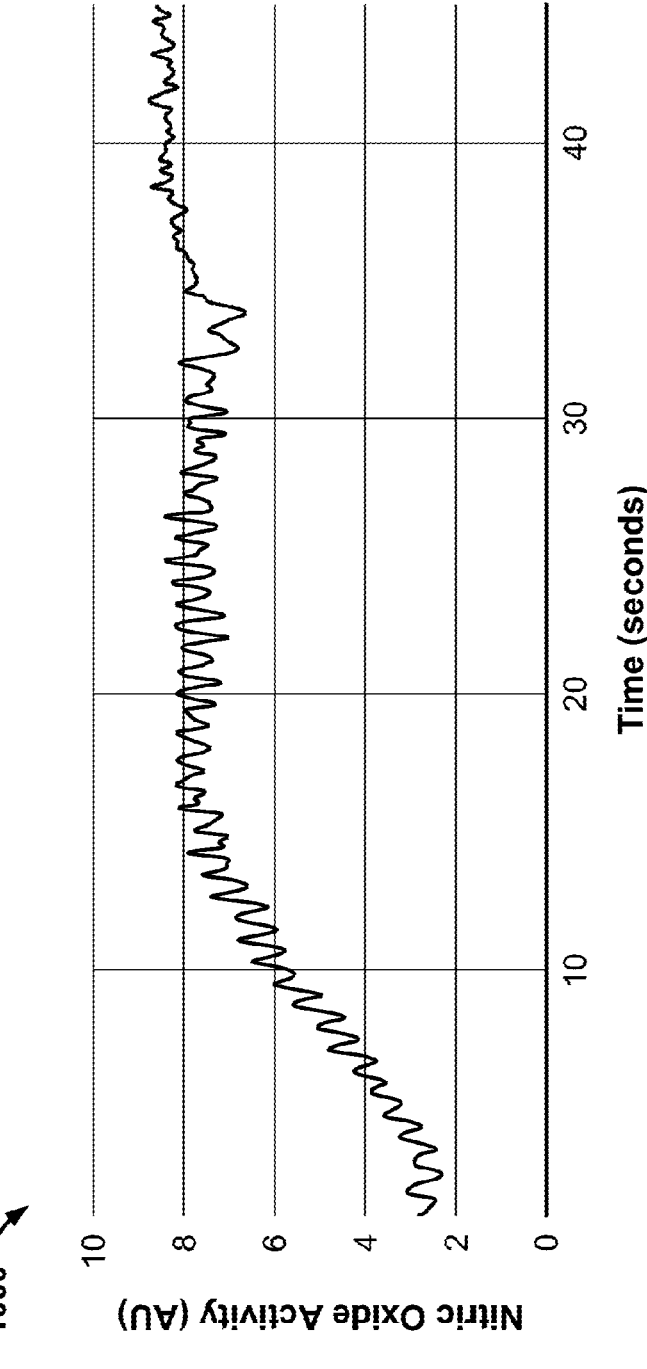
FIG. 10 is a graph illustrating an example of a non-invasive measurement of active nitric oxide in the blood of a subject during exercise according to some embodiments of the disclosure.

FIG. 10 is a chart 1000 demonstrating an individual's active nitric oxide, also known as s-nitrosothiol, level during exercise. The vertical axis represents the active nitric oxide level, and the horizontal axis represents the duration of exercise in seconds. Active nitric oxide levels at any given time point are represented on the graph by the solid black line. Active nitric oxide is a measurement of nitric oxide released from circulating red blood cells during exercise. Active nitric oxide dilates blood vessels, resulting in increased blood flow and oxygen delivery to the brain, heart, and exercising muscles. Thus, greater levels of active nitric are associated with elevated fitness, better cognitive health, and lower risk of Alzheimer's and cardiovascular disease. Additionally, by measuring a subject's active nitric oxide level during exercise one can determine the optimal type, volume, intensity, duration, and frequency of exercise to improve said biomarker parameter. Thus, enhancing a subject's health, fitness, and physical performance.

Figure 11:
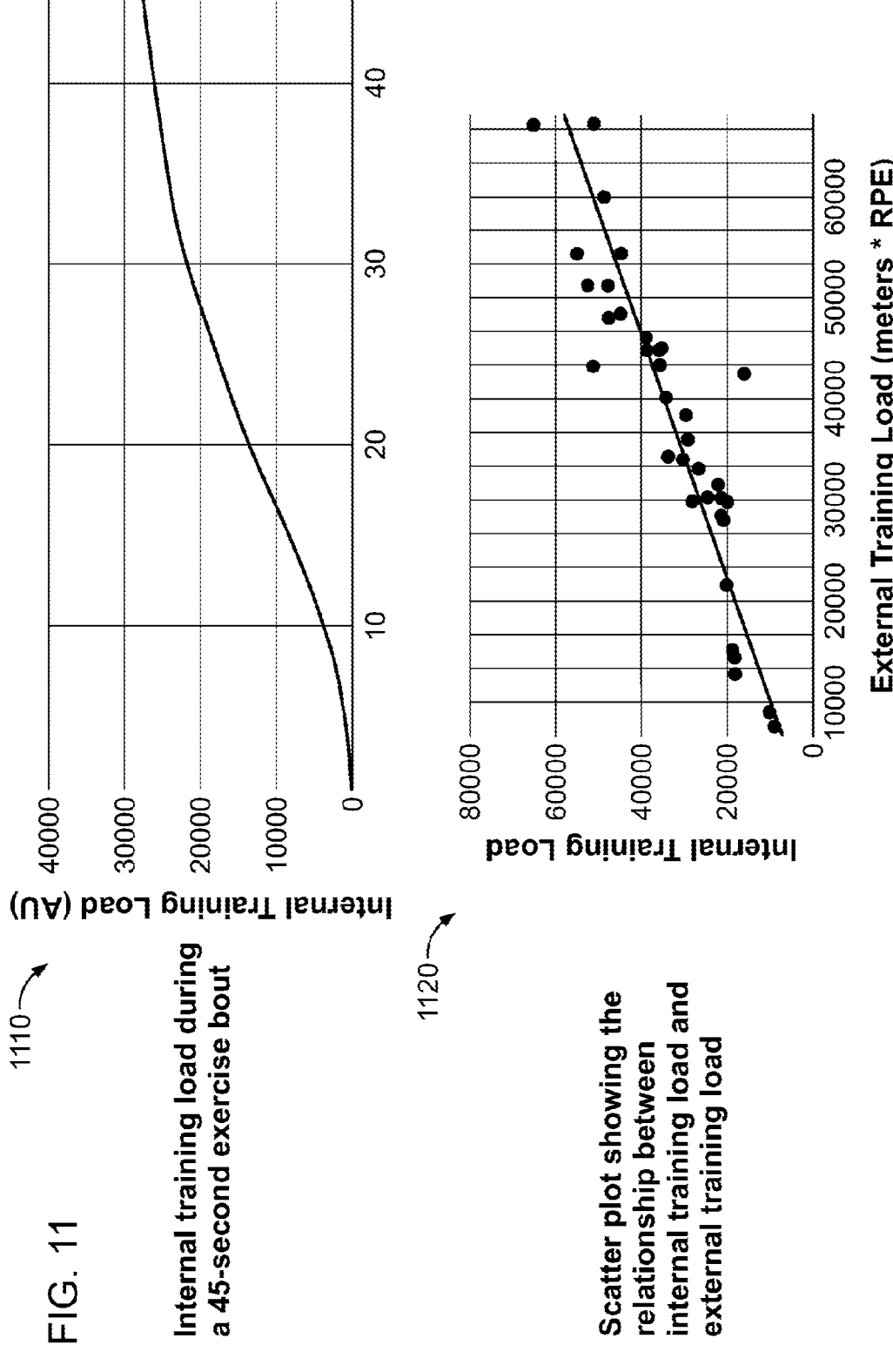
FIG. 11 is graph illustrating an example of a subject's internal training load (ITL) measurement during exercise and demonstrating the relationship between internal training load and external training load (ETL) according to some embodiments of the disclosure.

FIG. 11 is a chart 1110 demonstrating an individual's internal training load during exercise and demonstrating the relationship between internal training load and external training load (ETL) in scatter plot 1120. The vertical axis represents the internal training load, and the horizontal axis represents the duration of exercise in seconds. The internal training is represented by the solid black line on the graph. Internal training load (ITL) can only be quantified by isolating spectrophotometric measurements to the muscle tissue layer and its associated blood supply. The reason for this is that internal training load quantifies the total metabolic work performed by active skeletal muscles during exercise. Internal training load is strongly associated with external training load, defined as the amount of physical performed by a subject during exercise, as demonstrated in FIG. 8. However, it has many advantages over external training load. For example, internal training load (ITL) measurements can be used to quantity an individual's energy expenditure and total workload during exercise. Additionally, quantifying the internal training load allows individuals to reduce their risk of injury and personalize exercise training plans in an unprecedented manner, resulting in greater improvements in physical fitness.

Utilizing the embodiments described herein provides subjects with the ability to non-invasively measure a number of biomarker measurements in differentiated tissues layers and their associated blood supply. Specifically, measuring biological and physiological parameters in discrete locations within the body can provide unprecedented insights about a subject's health, fitness, and physical performance. Furthermore, the aforementioned biomarker measurements can be used to effect positive changes in a subject's physical state. For example, a subject may use the previously mentioned muscle oxygen consumption and active nitric oxide measurements to determine the optimal exercise type, volume, intensity, duration, and frequency to elicit desired physiological responses such as increased endurance, decreased risk of injury, or enhanced cognition.

Figure 12:
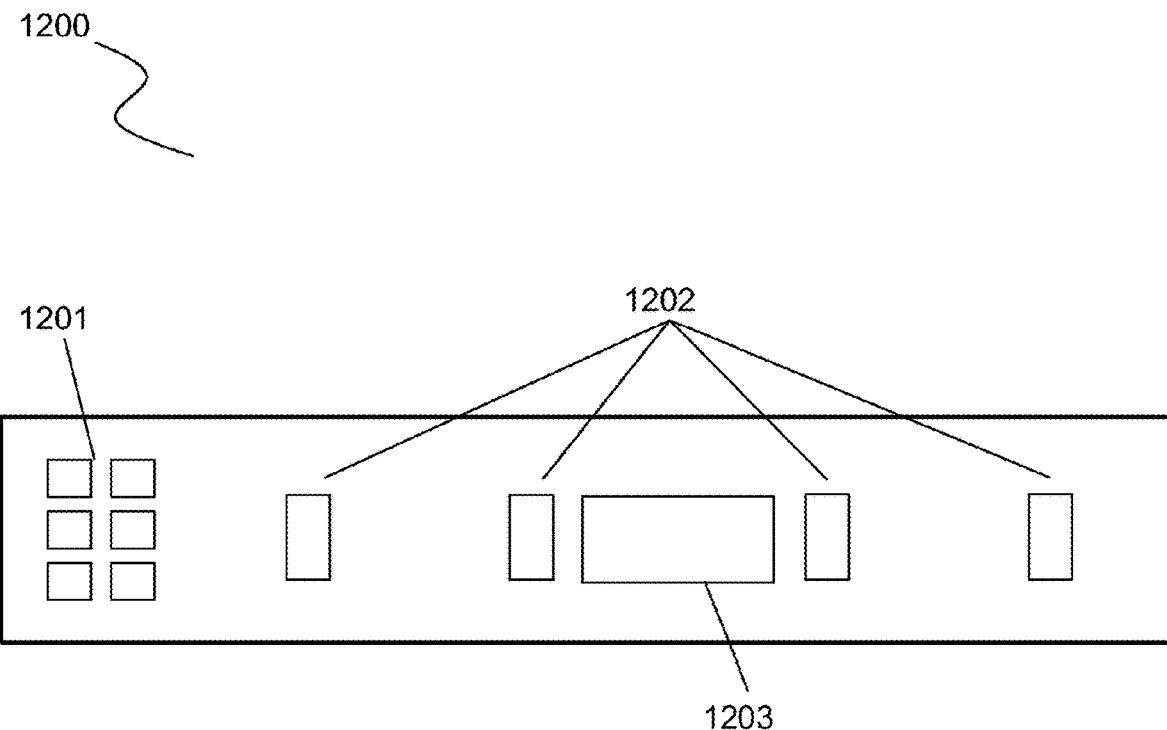
FIG. 12 illustrates an example measurement device according to some embodiments of the disclosure.

FIG. 12 illustrates an example measurement device 1200. The measurement device 1200, as described herein, can be wearable on a patient. For example, measurement device 1200 may be an embodiment of device 100 described above and may include the physical structures depicted in FIGS. 5 and 6, as described above. The measurement device 1200 can include one or more light sources 1201 (e.g., light emitting diodes, organic light emitting diodes, lasers, or a singular light source producing multiple wavelengths). For example, the light sources 1201 can include the LEDs 550-580 of the embodiment of FIG. 5. The one or more light sources 1201 can form an array. A control circuit and/or processor can control the one or more light sources 1201. For example, one or more of system 100 and/or system 200 may be embedded within, coupled to, or in communication with measurement device 1200. Accordingly, processor 112/214 can control the one or more light sources 1201. The one or more light sources 1201 may produce light at multiple wavelengths.

The measurement device 1200 can include one or more optical receivers 1202 (e.g., photodiodes or optical sensors). For example, the optical receivers 1202 can include the photodiodes 510-540 of the embodiment of FIG. 5. The one or more optical receivers 1202 can form an array. The one or more optical receivers 1202 can be placed a predetermined distances from the one or more light sources 1201. The one or more optical receivers 1202 can function as one or more of sensor(s) 102/202 of system 100 and/or 200. Information received from the one or more optical receivers 1202 can be converted in an analog to digital converter. The measurement device 1200 can include one or more processors for processing the data from the one or more optical receivers 1202 (e.g., processor 112/214). The measurement device 1200 can include a communication interface (e.g., Bluetooth®, WiFi, 5G, etc.) for communicating data to external systems and/or processors. The measurement device 1200 can include one or more memory devices for storing data (e.g., computer readable medium 110/212).

The measurement device 1200 can include a user interface comprising a display, haptics, and/or audio output 1203 for presenting data on the device. Alternatively, data can be presented on an external system. For example, the measurement device 1200 can communicate, through the communication interface, to a personal computer or mobile device, and output to a user through the personal computer or mobile device. In this example, the personal computer or mobile device may function as system 100 and/or 200. The external device can be configured to print at least a portion of the data.

The measurement device 1200 can include one or more additional sensing elements including, but not limited to: a thermometer and a bioimpedance sensor, which may be included among sensor(s) 102/202. The data collected by the additional sensing elements can provide enhanced measurement and post-processing analysis.

Operation of the measurement device 1200 can include initiating a data capture sequence. A data capture sequence can include activating the one or more light sources 1201 in a timed sequence of turning on and off. A data capture sequence can include activating the one or more optical receivers 1202, at predetermined distances, in conjunction with the activation of the one or more light sources 1201. Different wavelengths of generated light can be configured to target different substances within the body. Different predetermined distances between an optical receiver 1202 and light source 1201 can target different depths within the body. As an example, the light sources 1201 can be operated to emit light as described in detail above. The measurement device 1200 may capture the signals from the one or more optical receivers 1202. The captured signals can be preprocessed (i.e., run through an analog to digital converter and/or filtered). The captured signals can be converted into biomarkers. The biomarkers can be further processed, stored, and/or communicated (e.g., on device and/or to an external system). For example, the captured signal can be processed as described in detail above.

Figure 13:
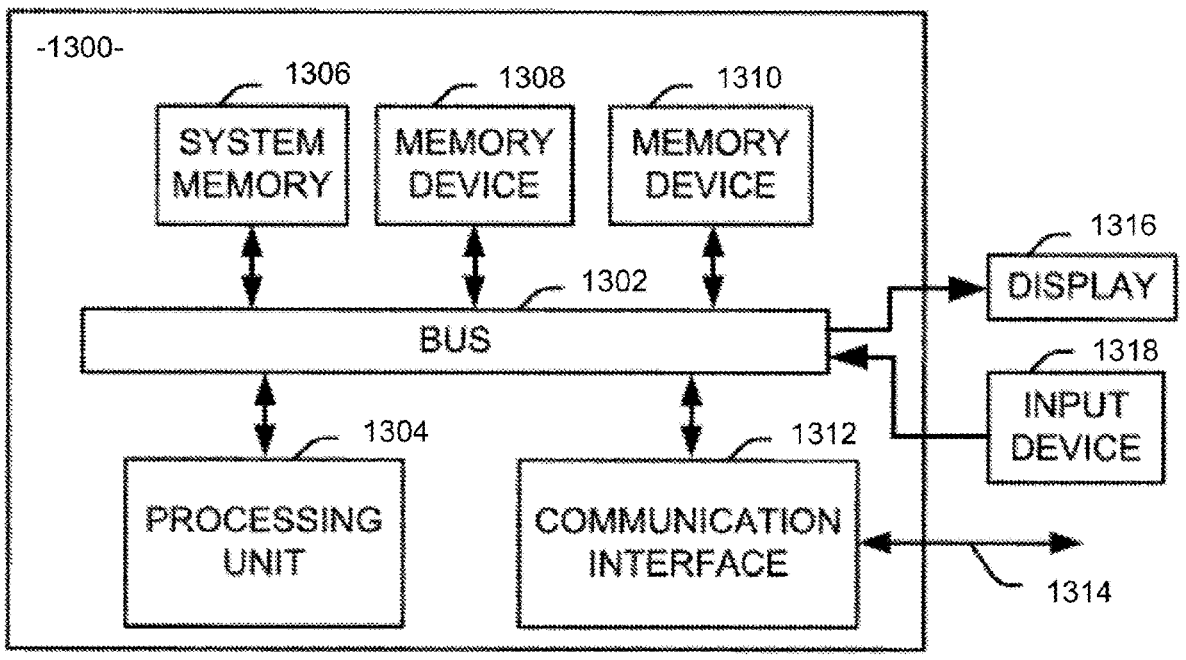
FIG. 13 is a schematic block diagram illustrating an example system of hardware components capable of implementing examples of the systems and methods disclosed herein.

FIG. 13 is a schematic block diagram illustrating an example system 1300 of hardware components capable of implementing examples of the systems and methods disclosed herein. The system 1300 can include various systems and subsystems. The system 1300 can include one or more of a personal computer, a laptop computer, a mobile computing device, a workstation, a computer system, an appliance, an application-specific integrated circuit (ASIC), a server, a server BladeCenter, a server farm, etc. In some embodiments, system 1300 may be part of, or may be in communication with, device 100 described above, and may include or be in communication with the physical structures depicted in FIGS. 5 and 6, as described above.

The system 1300 can include a system bus 1302, a processing unit 1304, a system memory 1306, memory devices 1308 and 1310, a communication interface 1312 (e.g., a network interface), a communication link 2214, a display 1316 (e.g., a video screen), and an input device 1318 (e.g., a keyboard, touch screen, and/or a mouse). The system bus 1302 can be in communication with the processing unit 1304 and the system memory 1306. The additional memory devices 1308 and 1310, such as a hard disk drive, server, standalone database, or other non-volatile memory, can also be in communication with the system bus 1302. The system bus 1302 interconnects the processing unit 1304, the memory devices 1306 and 1310, the communication interface 1312, the display 1316, and the input device 1318. In some examples, the system bus 1302 also interconnects an additional port (not shown), such as a universal serial bus (USB) port.

The processing unit 1304 can be a computing device and can include an application-specific integrated circuit (ASIC). The processing unit 1304 executes a set of instructions to implement the operations of examples disclosed herein. The processing unit can include a processing core.

The additional memory devices 1306, 1308, and 1310 can store data, programs, instructions, database queries in text or compiled form, and any other information that may be needed to operate a computer. The memories 1306, 1308 and 1310 can be implemented as computer-readable media (integrated or removable), such as a memory card, disk drive, compact disk (CD), or server accessible over a network. In certain examples, the memories 1306, 1308 and 1310 can comprise text, images, video, and/or audio, portions of which can be available in formats comprehensible to human beings.

Additionally, or alternatively, the system 1300 can access an external data source or query source through the communication interface 1312, which can communicate with the system bus 1302 and the communication link 1314.

In operation, the system 1300 can be used to implement one or more parts of a system in accordance with the present embodiments, such as the systems described in detail above. Computer executable logic for implementing the diagnostic system resides on one or more of the system memory 1306, and the memory devices 1308 and 1310 in accordance with certain examples. The processing unit 1304 executes one or more computer executable instructions originating from the system memory 1306 and the memory devices 1308 and 1310. The term "computer readable medium" as used herein refers to a medium that participates in providing instructions to the processing unit 1304 for execution. This medium may be distributed across multiple discrete assemblies all operatively connected to a common processor or set of related processors.

In some embodiments, the above-described systems and methods can be used in and/or with diagnostic systems, and more particularly, those related to non-invasive measurement of endogenous S-nitrosothiols. It will be appreciated by those of ordinary skill that the above-described systems and methods may be used to obtain and/or process measurements indicated below, for example.

Nitric oxide (NO) has been associated with many physiological effects, among them, smooth muscle relaxation, vasodilation, inflammation responses, and inhibition of platelet adhesion and aggregation. Finding the natural reservoirs of NO and finding ways to regulate the levels of biologically available NO and its alternative bioactive forms could provide a means to control these physiological effects. Nitric oxide (NO) and S-nitrosothiols (SNOs) are carried by hemoglobin together with oxygen. SNOs are a bioactive form of NO and the only endogenously active form of NO that can survive in blood, as NO itself cannot escape from red blood cells. SNO is released from hemoglobin in tissues, for example, when under hypoxia or during exercise, to dilate blood vessels and thereby oxygenate tissues. SNO released from RBCs thus controls microvascular blood flow in tissues and without this SNO tissues cannot oxygenate (Zhang PNAS 2015; Premont Circ Res 2019). SNO levels are thus a key component of VO2 (volume of oxygen consumed by tissues). While non-invasive means are available to detect oxygenated hemoglobin, no such means are available for detection of endogenous levels of NO or SNO.

The amount of oxygen consumed (VO2) by an individual is currently the gold standard measurement of fitness used by physicians and physiologists worldwide. VO2 represents the integrated capacity of the pulmonary, cardiovascular, and muscular system to uptake, transport, and consume oxygen. Traditional systems and methods for measuring VO2 are invasive and/or require carefully controlled conditions. For example, traditional VO2 measurements require the athlete to wear a mask in a lab, and the measurement tools can cost upwards of $35,000.

Embodiments described herein leverage the fact that nitric oxide release during exercise determines how much oxygen is available for muscles to use, and therefore monitor individuals' nitric oxide levels to determine fitness and/or other physiological characteristics. One value that can be measured, referred to as a personalized nitric oxide (PNO), is a measurement of how much active nitric oxide is released from circulating red blood cells during exercise. Active nitric oxide, represented by S-nitrosothiol in blood, opens up blood vessels that deliver oxygen to tissues, including the heart and brain, so a patient's nitric oxide level is strongly linked to their health. By monitoring this metric, and others described below, the system can determine how much nitric oxide an exerciser has released in response to exercise, as well as how intensely an exerciser needs to exercise, how long they should exercise, and what styles of exercise suit them best to provides improvements in fitness, performance, and health. The measured oxygen saturation with the small vessels in muscle is relative to the individual and the context, and thus the PNO metric derived from this measurement is relative across patients and context. It will be appreciated, however, that while the measurement may be relative, it is relative only to a degree, and that an individual's PNO measurement can be used as a reliable indicator of the individual's health and fitness.

The blood volume and oxygen saturation sensors used to calculate UO2 are portable, lightweight, and would less than five percent of many of the devices currently on the market for VO2 measurements. Further, the standard VO2 tests and measurement tools rely on expired gas concentrations to measure systemic oxygen consumption. However, by virtue of taking these central measurements, they miss out on important information like what metabolic processes are occurring in the muscle. As a result, they cannot reveal why an individual's VO2 maximum is not higher. Because the UO2 measurement is taken at the muscular level (and is influenced by nitric oxide concentrations), it not only measures oxygen consumption, but also allows determination of the rate limiting factors for increasing it (e.g. lack of blood flow or poor muscle use of oxygen). This not only provides a diagnostic measurement tool for fitness, but also indicates what exercise prescriptions are needed to improve health and fitness as well. For example, the origin of a change in UO2 can be determined from a time series of measurements and identified, as either a limitation in either oxygen supply, represented as restricted blood flow, or oxygen utilization, represented as a deficit of muscle function.

Figure 14:
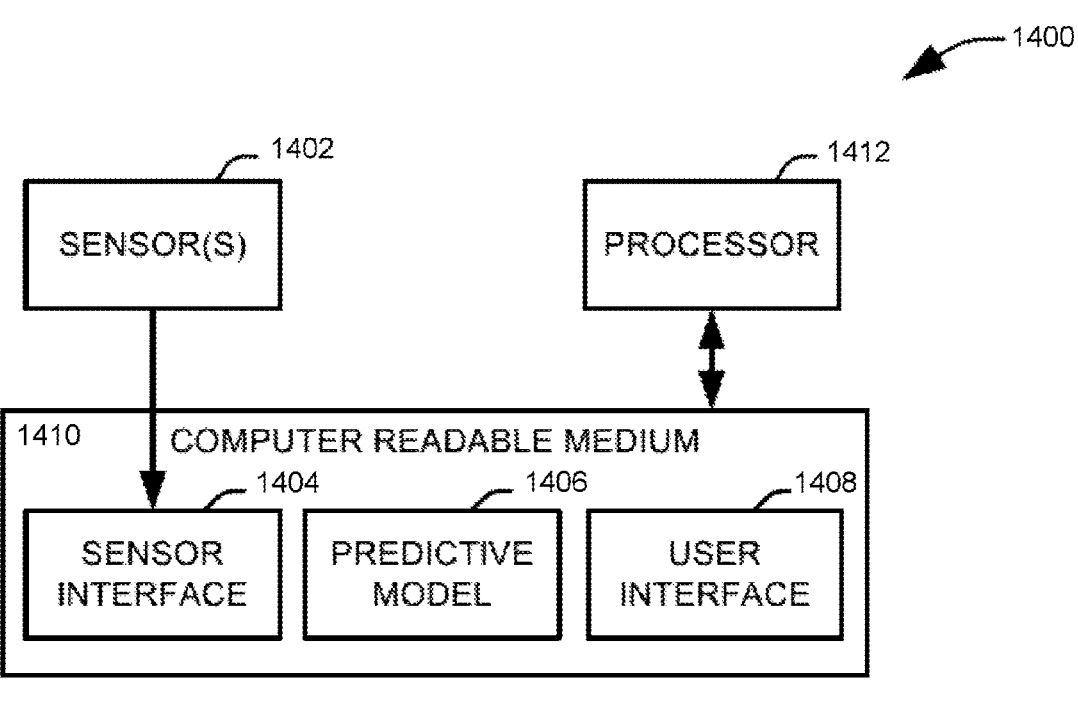
FIG. 14 illustrates an example of a system for generating a value representing an endogenous S-nitrosothiol content of tissue within a region of interest of a subject according to some embodiments of the disclosure.

FIG. 14 illustrates an example of a system 1400 for generating a value representing an endogenous S-nitrosothiol content of tissue within a region of interest of a subject. It will be appreciated that the system 1400 can determine the value representing an endogenous S-nitrosothiol content of tissue both non-invasively and in real-time. This can be used to match the S-nitrosothiol content of the tissue and derived metrics from this content to actions or biometric parameters of the subject during or after exercise or another physiological or external occlusion of blood flow from the muscle tissue. The system 1400 may include a set of at least one sensor 1402 that non-invasively measures a biometric parameter within the region of interest to provide at least one time series of measurements of the biometric parameter. In one example, where the biometric parameter includes blood volume and oxygen saturation, the set of sensors 1402 can include a single sensor that measures both blood volume and oxygen saturation or multiple sensors that collectively provide these measurements. In one implementation, a single optical sensor measures both oxygen saturation and blood volume using near-infrared spectroscopy, determining blood flow according to a change in total hemoglobin concentration and oxygen saturation. It will be appreciated that the set of sensors 1402 can include additional sensors that record multiple biometric parameters within the region of interest of the subject generally.

Each of a sensor interface 1404, a predictive model 1406, and a user interface 1408 may be implemented as machine readable instructions stored on a non-transitory computer readable medium 1410 and executed by an associated processor 1412. The sensor interface 1404 may receive the time series of measurements of the biometric parameter from the set of sensors 1402 and condition the data for use at the predictive model 1404. The predictive model 1404 can also utilize data about the subject that is stored at the computer readable medium 1410, including, for example, age, sex, genomic data, nutritional information, medication intake, and relevant medical history, as well as any other measured physiological parameters.

The predictive model 1410 can utilize one or more pattern recognition algorithms, each of which may analyze the data provided via the sensor interface 1404 and any additional data to assign a continuous or categorical parameter to the region of interest representing an amount of endogenous S-nitrosothiol present in the region of interest. Where multiple classification or regression models are used, an arbitration element can be utilized to provide a coherent result from the plurality of models. The training process of a given classifier will vary with its implementation, but training generally involves a statistical aggregation of training data into one or more parameters associated with the output class. For rule-based models, such as decision trees, domain knowledge, for example, as provided by one or more human experts, can be used in place of or to supplement training data in selecting rules for classifying a user using the extracted features. Any of a variety of techniques can be utilized for the classification algorithm, including support vector machines (SVM), regression models, self-organized maps, fuzzy logic systems, data fusion processes, boosting and bagging methods, rule-based systems, or artificial neural networks (ANN).

For example, an SVM classifier can utilize a plurality of functions, referred to as hyperplanes, to conceptually divide boundaries in the N-dimensional feature space, where each of the N dimensions represents one associated feature of the feature vector. The boundaries may define a range of feature values associated with each class. Accordingly, a continuous or categorical output value can be determined for a given input feature vector according to its position in feature space relative to the boundaries. In one implementation, the SVM can be implemented via a kernel method using a linear or non-linear kernel. A trained SVM classifier may converge to a solution where the optimal hyperplanes have a maximized margin to the associated features.

An ANN classifier may include a plurality of nodes having a plurality of interconnections. The values from the feature vector may be provided to a plurality of input nodes. The input nodes may each provide these input values to layers of one or more intermediate nodes. A given intermediate node may receive one or more output values from previous nodes. The received values may be weighted according to a series of weights established during the training of the classifier. An intermediate node may translate its received values into a single output according to a transfer function at the node. For example, the intermediate node can sum the received values and subject the sum to a rectifier function. The output of the ANN can be a continuous or categorical output value. In one example, a final layer of nodes provides the confidence values for the output classes of the ANN, with each node having an associated value representing a confidence for one of the associated output classes of the classifier. The confidence values can be based on a loss function such as a cross-entropy loss function. The loss function can be used to optimize the ANN. In an example, the ANN can be optimized to minimize the loss function.

Many ANN classifiers are fully connected and feedforward. A convolutional neural network, however, includes convolutional layers in which nodes from a previous layer are only connected to a subset of the nodes in the convolutional layer. Recurrent neural networks are a class of neural networks in which connections between nodes form a directed graph along a temporal sequence. Unlike a feedforward network, recurrent neural networks can incorporate feedback from states caused by earlier inputs, such that an output of the recurrent neural network for a given input can be a function of not only the input but one or more previous inputs. As an example, Long Short-Term Memory (LSTM)

networks are a modified version of recurrent neural networks, which makes it easier to remember past data in memory.

A rule-based classifier may apply a set of logical rules to the extracted features to select an output class. The rules may be applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees may be trained on random samples of the training set, and an average (e.g., mean, median, or mode) result across the plurality of decision trees is returned. For a classification task, the result from each tree would be categorical, and thus a modal outcome can be used.

The output of the predictive model 1406 can be a continuous parameter, representing an amount of endogenous S-nitrosothiol present in the region of interest, or a categorical parameter, representing, for example, an increase or decrease in the amount of endogenous S-nitrosothiol present in the region of interest or classes representing ranges of the amount. The output of the predictive model 1406 can be stored, for example, in an electronic health records database and/or provided to a user at an associated display via the user interface 1408.

Figure 15:
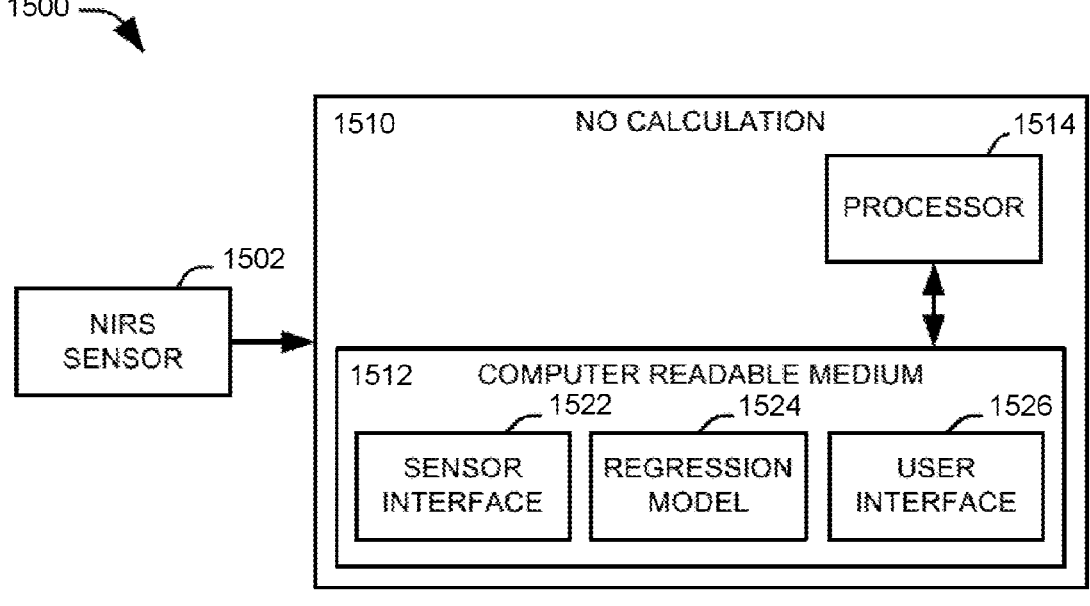
FIG. 15 illustrates another example of a system for generating a value representing an endogenous S-nitrosothiol content of tissue within a region of interest of a subject according to some embodiments of the disclosure.

FIG. 15 illustrates another example of a system 1500 for non-invasive, real-time generation of a value representing an endogenous S-nitrosothiol content of tissue within a region of interest of a subject. In one example, the tissue is muscle tissue, the endogenous S-nitrosothiol is the endogenous S-nitrosothiol generated from hemoglobin, and the amount of endogenous S-nitrosothiol is determined either during exercise of the muscle or after physiological or external occlusion of blood flow from the muscle tissue. The system 1500 may include a near-infrared spectroscopy (NIRS) sensor 1502 that non-invasively measures each of a blood volume and an oxygen saturation within the region of interest to provide a time series of blood volume measurements and a time series of oxygen saturation measurements. In one implementation, the time series of blood volume measurements can be represented as a time series for a total hemoglobin metric. A spectroscopy sensor can include a strap such that the sensor is strapped against the skin. The strap can be flexible and/or elastic. As an example, the sensor can be incorporated into a wristband. A person of ordinary skill in the art will recognize that a strap or any other clothing element may be configured to interface a measurement device, as described herein, to any relevant region of interest.

A nitric oxide (NO) calculation assembly 1510 may be implemented as machine readable instructions stored on a non-transitory computer readable medium 1512 and executed by an associated processor 1514. The NO calculation assembly 1510 may include a sensor interface 1522, a regression model 1524, and a user interface 1526. The sensor interface 1522 may receive the time series of blood volume measurements and the time series of oxygen saturation measurements from the NIRS sensor and condition the data for use at the regression model 1524.

The regression model 1524 may determine a relationship between the time series of blood volume values and the time series of oxygen saturation values and provide at least one parameter representing the determined relationship. In one example, the relationship is linear, and the ordered pairs provided by the two time series can be fitted to a line of best fit. In this example, the provided parameter is the slope of the line of best fit, with an amount of endogenous S-nitrosothiol in the tissue being derived from the slope. In another example, the parameter is derived from a correlation coefficient between oxygen saturation and blood volume. This value can then be provided to a user via the user interface 1526. In one example, instead of or in addition to displaying the value directly, the value can be used for real-time calculation of other metrics representing the health and fitness of the subject.

Figures 16, 17:
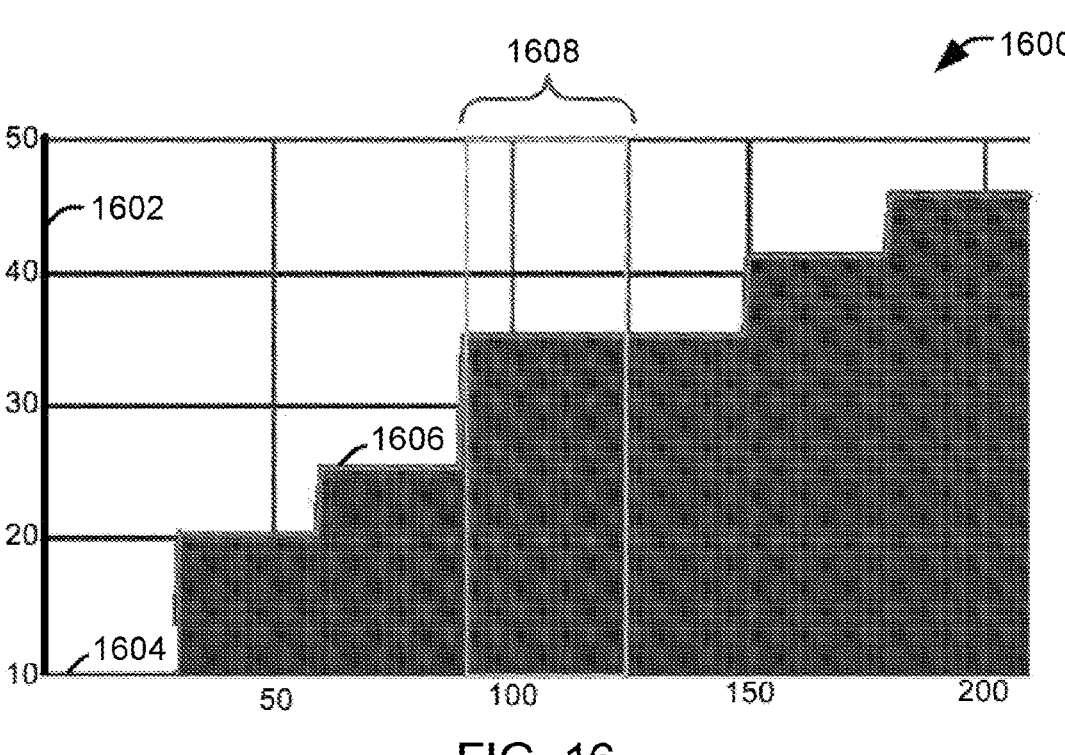
FIG. 16 is a chart illustrating a PNO level for a patient during exercise according to some embodiments of the disclosure.
FIG. 17 is a chart illustrating a VO2 level for a patient during exercise according to some embodiments of the disclosure.

FIG. 16 is a chart 1600 illustrating a PNO level for a patient during exercise. The vertical axis 1602 represents the PNO level, and the horizontal axis 1604 represents a duration of exercise in seconds, with the PNO level at each time indicated as a shaded area 1606 on the graph. A rest period 1608 was given to the patient around one hundred seconds, and it can be seen that the PNO level 1606 stayed level during this period and for a short period thereafter.

As noted above, VO2 is the gold standard measure of fitness used by physicians. Traditionally, VO2 measurement requires invasive testing and expensive lab equipment, but the system 1500 allows this measurement to be made non-invasively, within local tissues, making it available during activities of daily living (defined as UO2). FIG. 17 is a chart 1700 illustrating a UO2 level for a patient during exercise. The vertical axis 1702 represents the UO2 level, and the horizontal axis 1704 represents a duration of exercise in seconds, with the UO2 level at each time indicated as a shaded area 1706 on the graph. A rest period 1708 was given to the patient around one hundred seconds, and it can be seen that the UO2 level 1706 fell sharply during the rest period.

Figure 18:
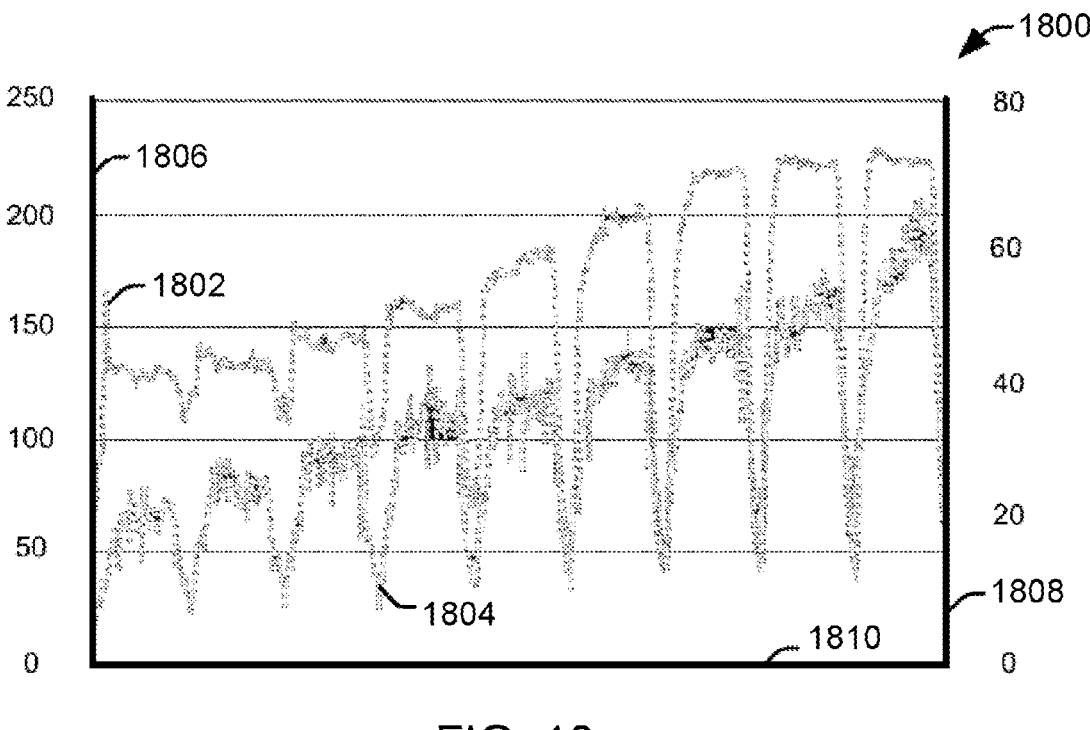
FIG. 18 depicts a chart of a time series of UO2 measurements and a time series of VO2 measurements for an athlete operating a full-body exercise bike using one sensor for recording blood volume and oxygen saturation according to some embodiments of the disclosure.
Figure 19:
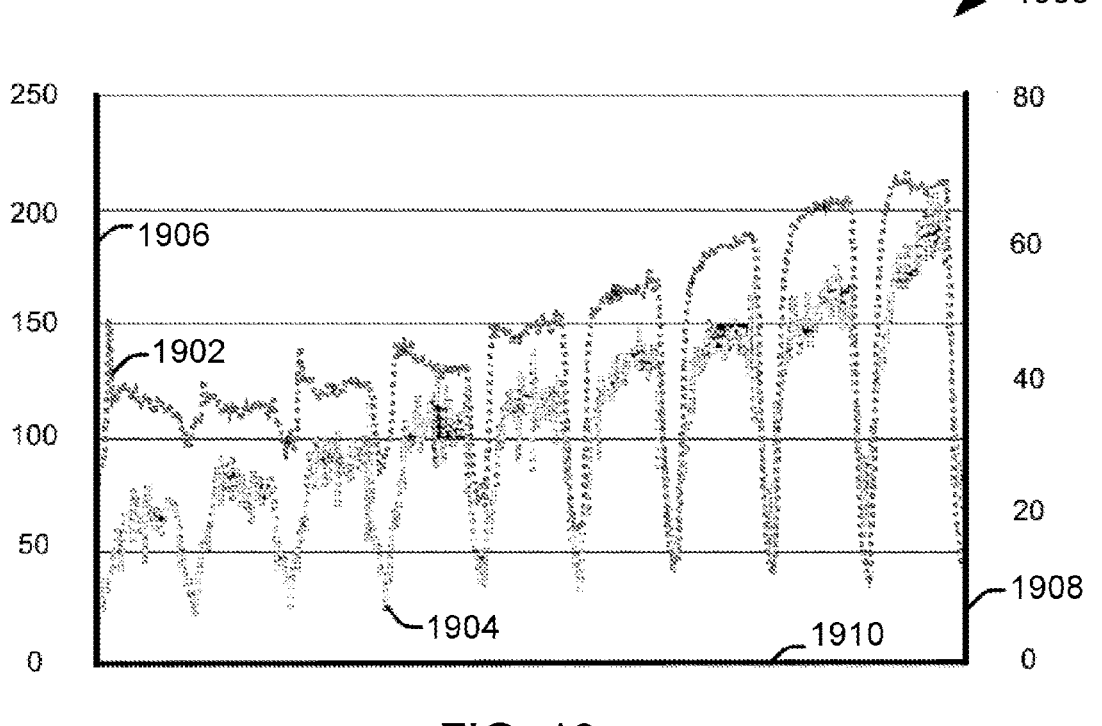
FIG. 19 depicts a chart of a time series of UO2 measurements and a time series of VO2 measurements for an athlete operating a full-body exercise bike using one sensor for recording blood volume and oxygen saturation according to some embodiments of the disclosure.

UO2 measurement is a nitric oxide related measure of local muscle oxygen consumption, created to behave in the same way as a true VO2 measure. Specifically, UO2 can be generated as a function of the localized nitric oxide measurement and the blood flow to represent a measure of usable oxygen available for the muscle tissue in a region of interest. As shown in FIGS. 18 and 19, the UO2 measurement is an excellent proxy for VO2, and UO2 can be measured using sensors having a cost of about one-hundredth of the cost for even low-end VO2 measurement devices.

FIG. 18 depicts a chart 1800 of a time series of UO2 measurements 1802 and a time series of VO2 measurements 1804 for an athlete operating a full-body exercise bike using one sensor for recording blood volume and oxygen saturation. The left vertical axis 1806 represents VO2 in units of mL/kg/min, the right vertical axis 1808 represents UO2, in arbitrary units, and the horizontal axis 1806 represents elapsed time. A very strong correlation (r=0.95) can be seen between the measured UO2 1802 and the measured VO2 1804. From this it should be clear that the estimated VO2 maximum can be deduced from the UO2 measurement. The estimated VO2 maximum in this figure is 68 ml/kg/min, as derived from the UO2.

Similarly, FIG. 19 depicts a chart 1900 of a time series of UO2 measurements 1902 and a time series of VO2 measurements 1904 for an athlete operating a full-body exercise bike using two sensors, on different limbs, for recording blood volume and oxygen saturation. The left vertical axis 1906 represents VO2 in units of mL/kg/min, the right vertical axis 1908 represents UO2, in arbitrary units, and the horizontal axis 1910 represents elapsed time. An extremely strong correlation (r=0.95) can be seen between the measured UO2 1902 and the measured VO2 1904.

Active nitric oxide levels reflect the supply of oxygen: the better the supply and utilization of oxygen the better the performance. MAX-NO Power and MAX-NO Endurance are nitric oxide related measurements that can be generated by the system that strongly correlate with an individual's real power output and maximal endurance levels.

Figure 20:
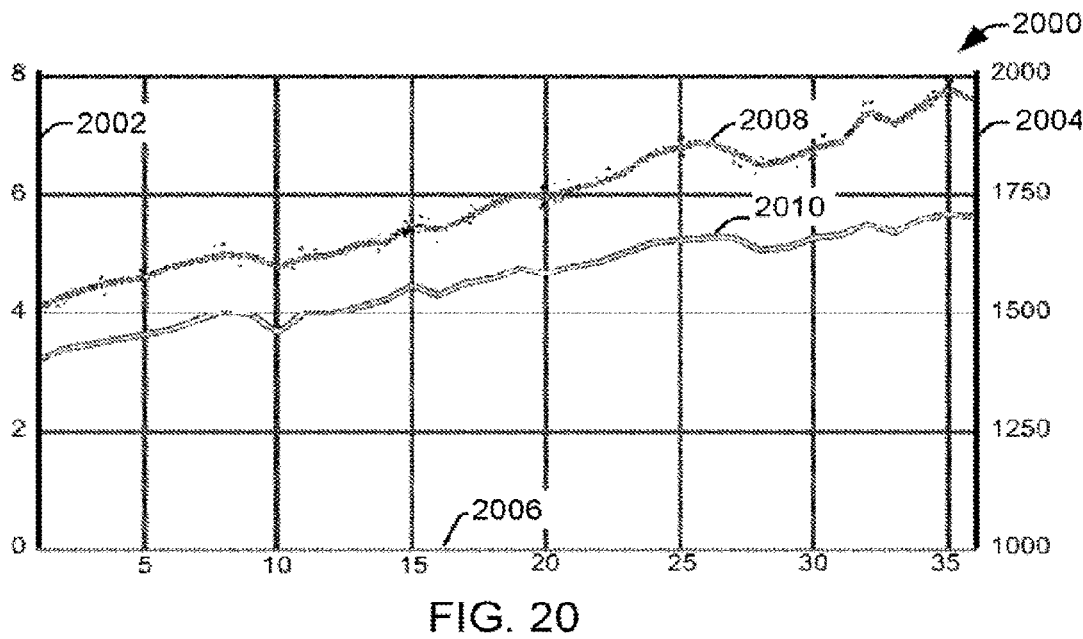
FIG. 20 depicts a chart of an athlete's MAX-NO Power, recorded weekly over a six-month period according to some embodiments of the disclosure.

FIG. 20 depicts a chart 2000 of an athlete's MAX-NO Power, recorded weekly over a six-month period. The left vertical axis 2002 represents the MAX-NO Power in arbitrary units, the right vertical axis 2004 represents the maximum power output for the athlete, in watts, and the horizontal axis 2006 represents the elapsed time, in weeks. As the athlete increases their fitness, measured by increases in maximal power output 2008 in wattage, their MAX-NO Power 2010 increases as well. A very strong correlation (R2=0.95) between the measured MAX-NO Power 2010 and maximal power output 2008 in watts, establishes MAX-NO Power as an excellent biomarker of performance.

Figure 21:
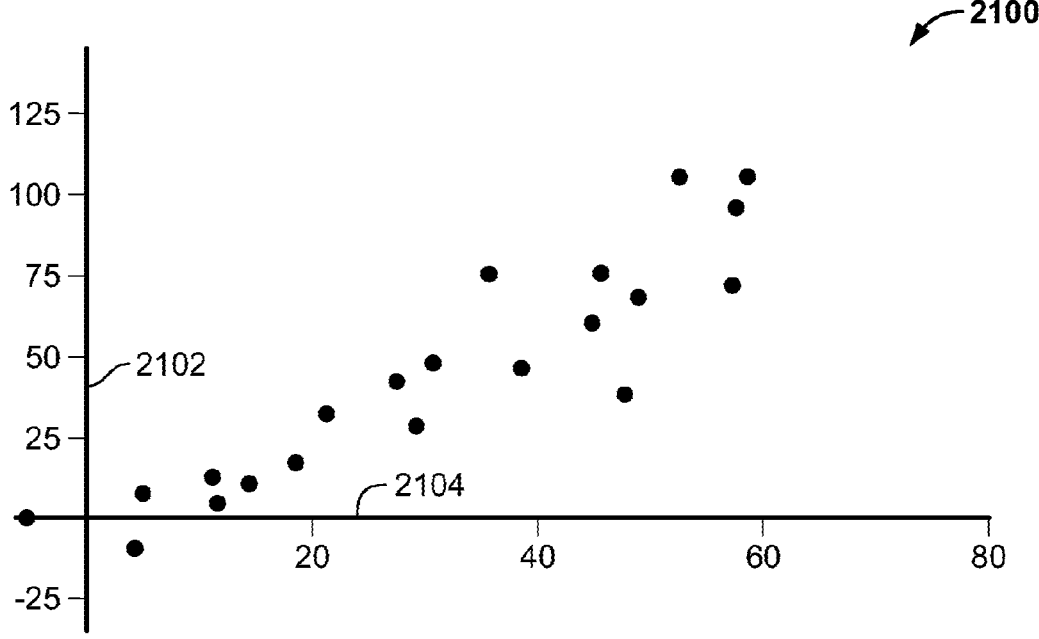
FIG. 21 depicts a chart illustrating a relationship between an athlete's MAX-NO Endurance and their critical power, recorded over a six-week period, as a scatterplot according to some embodiments of the disclosure.

FIG. 21 depicts a chart 2100 illustrating a relationship between a MAX-NO Endurance improvement for a group of twenty-one athletes and their critical power (a gold standard for endurance, measured in watts), recorded over a six-week period, as a scatterplot. The vertical axis 2102 represents a percentage improvement in MAX-NO Endurance for the twenty-one athletes, and the horizontal axis 2104 represents the improvement in critical power for the athletes, in watts. As can be seen from the chart, there is a significant correlation between improvement in MAX-NO Endurance and improvement in critical power, establishing MAX-NO Endurance as a non-invasive measure of endurance.

It will be appreciated that specific exercises and other therapies can be prescribed to a patient based upon their values for these metrics. For example, an individual whose Max-NO power is high, compared to their Max-NO endurance, is capable of extracting oxygen from the blood and utilizing it in the skeletal muscle at a greater rate that it can be delivered. These individuals will see the best gains in their exercise regime by performing lower intensity, longer duration, exercise in a continuous fashion. For example, Mr. Jones, a twenty eight year old with a Max-NO power of 6 and a Max-NO endurance of 3, could be prescribed three days a week of a twenty minute run at 50-55% of his Maximum UO2. This would be expected to improve his Max-NO Endurance over the course of several weeks.

Alternatively, an individual whose Max-NO endurance is high, compared to their Max-NO power, is capable of supplying oxygen to the working muscles at a much faster rate than they can extract it from the blood and utilize it for energy production. These individuals will see the best gains in their exercise regime by performing high intensity, short duration, work bouts with rest periods interspersed between them. In these instances, there will be very large acute increases in UO2 with relative low points between exercise bouts. For example, Mrs. Benneton, a forty-eight year old cyclist with a Max-NO endurance of 7 and a Max-NO power of 2.5, could be prescribed two days a week of sprinting at a near maximal intensity until her UO2 stops rising then resting for three minutes, repeating for six sets. This would be expected to improve both her Max-NO Power and max UO2 over the course of several weeks.

In another example, an individual whose upper body PNO levels are high compared to their lower body PNO levels will be instructed to redistribute their power output such that they decrease the amount of work their upper body is doing and increase the amount of work their lower body is doing.

By doing so they will increase PNO levels in their lower body, leading to a greater full body PNO value which can be sustained for a longer duration. This will increase the delivery of oxygen to brain, heart and muscles. In another example, an individual suffering from early onset Alzheimer's Disease can be assigned exercises to improve their PNO level, and this improve blood flow to the brain. For example, Mrs. Levy, a seventy-year-old with early onset Alzheimer's disease could be prescribed daily exercise of thirty minutes of walking with the goal of increasing her PNO of 5. Mrs. Levy could be prescribed a thirty minute daily bicycle routine that is titrated such that her PNO increases to 15 over the course of the workout. At six months, improvement of both her memory and her baseline PNO would be expected.

As discussed, VO2 is currently the gold standard measurement of fitness used by physicians and physiologists worldwide and represents the integrated capacity of the pulmonary, cardiovascular, and muscular system to uptake, transport, and consume oxygen. UO2 measurement is a nitric oxide related measure of local muscle oxygen consumption, created to behave in the same way as a true VO2 measure. Specifically, UO2 can be generated as a function of the localized nitric oxide measurement and the blood flow to represent a measure of usable oxygen available for the muscle tissue in a region of interest. As shown in FIGS. 5 and 6, the UO2 measurement is an excellent proxy for VO2.

Individuals with Alzheimer's Disease are known to have low VO2. VO2 largely depends on microvascular blood flow and nitric oxide from red blood cells controls blood flow. Thus, it stands to reason that the nitric oxide-based measurement described herein as UO2, tracks VO2 and therefore PNO can be used to predict VO2 max in an individual. Therefore, in another embodiment, the invention provides a method of determining a risk of Alzheimer's Disease or early onset disease by using UO2 as a biomarker. If one improves their UO2 (and PNO), there would be an improvement or protection against the Alzheimer's Disease. In one aspect, the invention provides a method of determining a risk for diseases that associate with reduced blood flow, for example, dementia or other reductions in cognitive function associated with blood flow or cardiovascular/cardiometabolic disease. An individual with Alzheimer's Disease, for example, is prescribed an exercise regimen and their UO2 measurements are taken over time to determine improvement in the disease. For example, UO2 is measured at a beginning time point before an exercise regimen is commenced and measured at a second time point (and optionally further time points) to determine if there is an increase in the UO2 value, reflecting an improvement of cognitive function or dementia, for example. Other complementary tests can be used including cognitive tests known to those of skill in the art to further assess improvement in the disease state of the individual.

In another example, Mr. Jack is a sixty-year-old businessman with heart disease. He could be prescribed a daily exercise regime of thirty minutes to improve his PNO level of 13. In this example, his exercise regime could be increased to forty minutes over time with a doubling of PNO, representing an increased ability to provide oxygenated blood to the heart muscle. In another example, Mrs. Stevenson is a sedentary mother with three young children who she struggles to keep up with in daily living with a Maximum UO2 of 43. She was prescribed an exercise regime consisting of two days per week, with the first day including twenty to thirty minutes of moderate intensity exercise at 50-60% of her Maximum UO2 and the second day including three five-minute exercise bouts at 75¬5% of her Maximum UO2. This would be expected to increase her fitness and energy, as well as her maximum UO2. Likewise, in another example, Mr. James is a sixty-year-old businessman with diabetes. His baseline blood sugar was 200. He could be prescribed a daily exercise regime of 20 minutes to improve his PNO level of 12. In this example, his exercise regime could be increased to forty minutes over time with a doubling of PNO, representing an increased ability to provide oxygenated blood to muscles and reduce his resting blood sugars.

In view of the foregoing structural and functional features described above, example methods will be better appreciated with reference to FIGS. 22-24. While, for purposes of simplicity of explanation, the example methods of FIGS. 22-24 are shown and described as executing serially, it is to be understood and appreciated that the present examples are not limited by the illustrated order, as some actions could in other examples occur in different orders, multiple times and/or concurrently from that shown and described herein. Moreover, it is not necessary that all described actions be performed to implement a method. Each of these methods can be performed by system 1400 of FIG. 14 and/or system 1500 of FIG. 15, for example.

FIG. 22 illustrates one example of a method 2200 for generating a value representing an endogenous S-nitrosothiol content of tissue within a region of interest of a subject. At 2202, a biometric parameter may be measured non-invasively by sensor(s) 1402/1502 within a region of interest of a subject to provide a time series of measurements of the biometric parameter. In one example, these measurements are taken while the subject is engaging in exercise. In another example, these measurements are taken during a rest period after the subject has engaged in exercise. In a further example, the measurements can be taken immediately after a physiological or external occlusion of blood flow to the region of interest or after physiological depletion of oxygen. In one implementation of this example, an overshoot response in one of blood flow and oxygen saturation above baseline following an induced hypoxia is measured to provide one of the time series of oxygen saturation measurements and the time-series of blood volume measurements, the predictive model using the overshoot or rate value to generate a value representing an endogenous S-nitrosothiol content of tissue within the region of interest.

At 2204, a value representing an endogenous S-nitrosothiol content of tissue within the region of interest may be generated by processor 1412/1514 from the time series via a predictive model 1406/224. In one implementation, a linear relationship between a first time series, representing blood volume, and a second time series, representing oxygen saturation, is determined, and the value is determined according to this linear relationship. For example, the two time series can be provided to a linear regression model to provide a best-fit line between the oxygen saturation and the blood volume over time, with the value representing the endogenous S-nitrosothiol content of tissue within the region of interest being derived from a slope of the best-fit line. At 2206, the value representing an endogenous S-nitrosothiol content of tissue within the region of interest may be stored by processor 1412/1514 in a memory implemented as a non-transitory computer readable medium 1410/1512. In one example, the method 2200 can be performed before and after a therapy provided to the subject to determine an effect of the therapy on the endogenous S-nitrosothiol content within the region of interest by comparing a value generated after the therapy compared to a stored value generated before the therapy. The stored value can also be used to generate one or more of a maximum nitric oxide endurance metric, a maximum nitric oxide power metric, a usable oxygen consumption metric, and a personalized nitric oxide metric for the subject.

FIG. 23 illustrates another example of a method for generating a value representing an endogenous S-nitrosothiol content of tissue within a region of interest of a subject. At 2302, blood volume and oxygen saturation within a region of interest of a subject may be measured by sensor(s) 1402/1502 non-invasively to provide a first time series of oxygen saturation measurements and a second time series of blood volume measurements. For example, both blood volume and oxygen saturation in the tissue can be determined via near-infrared spectroscopy. In one example, these measurements are taken while the subject is engaging in exercise. At 2304, a linear relationship between the first time series and the second time series may be determined by processor 1412/1514 via a predictive model 1406/224. For example, the two time series can be provided to a linear regression model to provide a best-fit line between the oxygen saturation and the blood volume over time.

At 2306, a value representing an endogenous S-nitrosothiol content of tissue within the region of interest may be generated by processor 1412/1514 from the linear relationship between the first time series and the second time series. In one implementation, in which the linear relationship is represented as a best-fit line between the first time series and the second time series, the value representing the endogenous S-nitrosothiol content of tissue within the region of interest can be derived from a slope of the best-fit line. At 2308, the value representing an endogenous S-nitrosothiol content of tissue within the region of interest may be stored by processor 1412/1514 in a memory implemented as a non-transitory computer readable medium 1410/1512. The stored value can also be used to generate one or more of a maximum nitric oxide endurance metric, a maximum nitric oxide power metric, a usable oxygen consumption metric, and a personalized nitric oxide metric for the subject.

FIG. 24 illustrates a further method 2400 for generating a value representing an endogenous S-nitrosothiol content of tissue within a region of interest of a subject. At 2402, a subject is instructed to engage in aerobic exercise. In one example, a subject could be instructed to cycle an exercise bike. At 2404, blood volume and oxygen saturation within a region of interest of a muscle of the subject that is impacted by the exercise may be measured non-invasively by sensor(s) 1402/1502 to provide a first time series of oxygen saturation measurements and a second time series of blood volume measurements.

At 2406, at least one of the time series of blood volume and the time series of oxygen saturation within a region of interest may be conditioned by processor 1412/1514 to remove extraneous influences. Blood flow in tissues is mediated by many different factors, including prostaglandins, catecholamines, nitric oxide, temperature, kinins, adenosine triphosphate (ATP), hypoxia, and similar factors. For example, kinins regulate flow increases during inflammation and NO mediates shear and Ach induced vasodilation. To facilitate measurement of the effects of NO released from hemoglobin on blood flow, the collected blood flow data can be conditioned to remove the effects of these factors. For example, most aerobic exercise involves repeated contraction of the muscle on a somewhat predictable period. This reduction of blood volume can be quantified as a periodic signal, represented as another time series, which can be removed from the time series of blood volume measurements. Other physiological influences on one or both of the blood volume and the oxygen saturation will vary with the location and the specific exercise, and these non-linear influences on the relationship between blood volume and oxygen saturation can be identified and removed from the time series by adding signals representing these influences.

At 2408, a statistical process may be performed by processor 1412/1514 to identify a linear relationship between the blood flow, as derived from the time series of blood volume measurements, and the oxygen saturation, and a value representing an endogenous S-nitrosothiol content of tissue within the region of interest is generated from the linear relationship. For example, a linear regression analysis can be performed, and the slope of a best-fit line generated in the regression analysis can be used to quantify the linear relationship between the blood flow and the oxygen saturation. A correlation coefficient between the two parameters can also be generated and used to evaluate the linear relationship where the muscle is particularly depleted of oxygen and the slope cannot be readily established. At 2410, the value representing an endogenous S-nitrosothiol content of tissue within the region of interest may be stored by processor 1412/1514 in a memory implemented as a non-transitory computer readable medium 1410/1512.

Figures 25, 26:
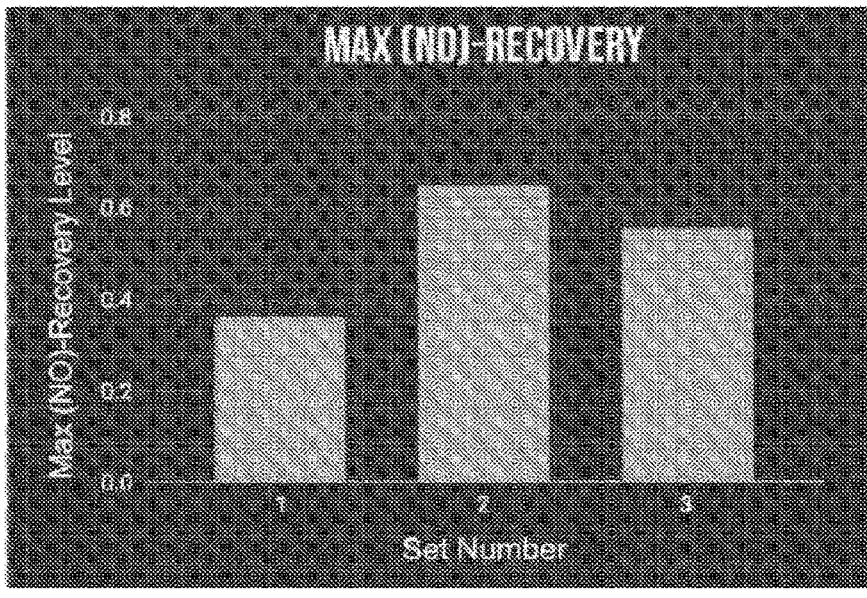
FIG. 25 depicts metrics and use cases for professional sports platform using (NO) according to some embodiments of the disclosure.
FIG. 26 depicts a bar graph of athlete recovery measure as Max (NO)-Recovery Level at three set numbers according to some embodiments of the disclosure.

FIG. 25 illustrates metrics and use cases for professional athletes. Specific metrics can correlate to different positive athletic outcomes such as the improvements in maximal speed, power, or endurance. Additionally, metrics may aid in monitoring, predicting, and planning an athlete's recovery and regeneration. For example, measurements of Nitric Oxide can be used to assist in developing exercise activities that cause the maximum endogenous increase in Nitric Oxide in a person's blood supply. In another example, Nitric Oxide recovery can be monitored to determine how much rest the athlete needs in-game or between sets. In a third example, Nitric Oxide regeneration can be monitored and/or improved through targeted exercise to reduce injury risk and expedite return to play from injury.

FIG. 26 depicts an example measurement of MAX NO Recovery versus the number of sets performed in exercise routine. Max (NO)-Recovery is derived from the rate of reoxygenation in a muscle tissue following an exercise bout, and it is influenced by various factors such as (NO) concentrations, breathing patterns, and aerobic fitness levels. Max (NO)-recovery can tell an athlete how recovered they are in live time, as well as when they are fully recovered after an exercise bout. Additionally, individuals can train to increase their Max (NO)-Recovery scores, which will allow them to recover quicker after or between exercise bouts. As noted in the chart, the athlete's MAX NO Recovery peaks at two sets. A threshold can be set for a drop from the peak MAX NO Recovery to determine a maximum amount of sets the athlete should perform. Through conditioning, an athlete may achieve peak at a greater number of sets and/or the drop rate after the peak value may lessen.

Figure 27:
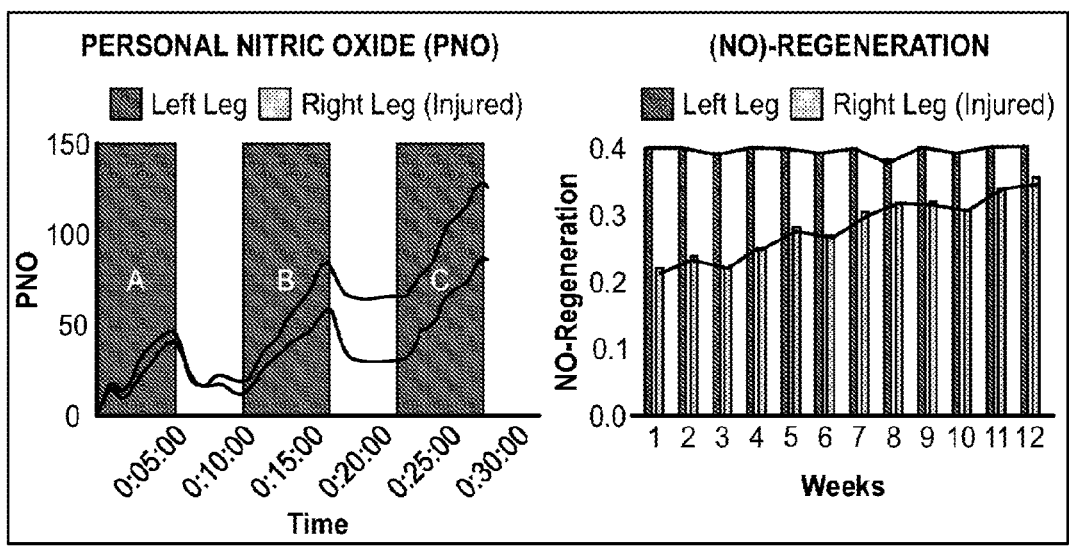
FIG. 27 illustrates personal nitric oxide (PNO) overtime and (NO)-regeneration over time according to some embodiments of the disclosure.

FIG. 27 depicts an example measurement of PNO and MAX NO Regeneration over time. The PNO measurement charts an athlete during an exercise session through alternating periods of work and rest. While the athlete exercises, PNO increases. During a recovery period, PNO drops back down. The more PNO the athlete generates, the better their health and performance. PNO can also be used to mitigate injury risk and decrease an individual's risk of re-injury during rehabilitation. PNO levels can be compared between a healthy and injured leg which informs the athlete about their ability to handle loading.

By comparing an injured person's level of Nitric Oxide taken at different times, one may determine the level of tissue injury recovery that the injury repair has made relative to a total recovery. The measurement for MAX NO Regeneration can be calculated at rest. To record Max NO Regeneration a cuff can be placed on an individual's upper arm or upper thigh, then the biosensor can be placed on a large muscle distal to the cuff. The cuff can be inflated until the pressure occludes blood flow to the limb. Once blood flow is occluded the individual can remain stationary with the cuff inflated for a fixed time period, after which the cuff may automatically deflate, allowing blood to flow back into the limb. Biomarker measurements can be recorded during the post ischemia reperfusion period and can be used to calculate NO levels.

In the example measurement, the athlete's MAX NO regeneration scores are depicted on their left and right leg for 12 weeks after receiving right ACL surgery. The difference between the healthy left leg and injured right leg are easily trackable throughout the recovery process. The metric can be used in combination with existing metrics, such as strength. The metric can be used to optimize a player's training regimen to get them back on field as quickly as possible without undue risk of injury.

Figure 28:
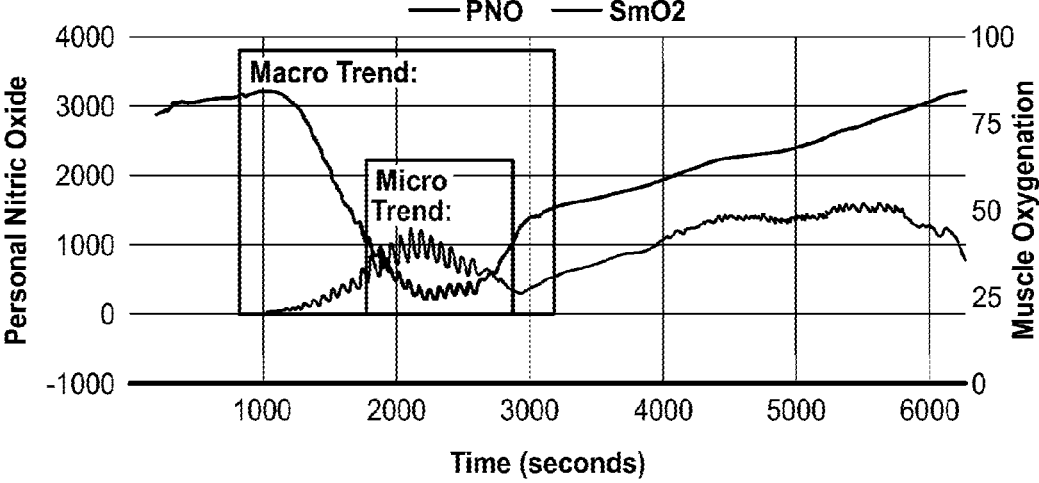
FIG. 28 depicts a graph demonstrating the effects of exercise on muscle oxygenation (SmO2) and s-nitrosothiols (PNO) according to some embodiments of the disclosure.

As seen in FIG. 28, there are separate trends occurring simultaneously, when measuring PNO or muscle oxygenation (SmO2). The macro trend represents the autoregulation of blood flow. When oxygen is utilized in the skeletal muscle there is a compensatory increase in muscle blood flow. When this occurs an inverse linear correlation can be observed between muscle oxygenation and total hemoglobin (THb), which is a measure of muscle blood volume (not depicted). As a result, a gross increase in nitric oxide and s-nitrosothiols (PNO) can be observed. This response can last seconds to minutes.

The micro trend represents active hyperemia. When a muscle is contracted, blood flow is restricted, and as a result, oxygen levels decline. Then, during the muscle's relaxation phase before the next contraction, blood flow increases and oxygen saturation goes up. During active hyperemia SmO2 and THb are linearly correlated. The active hyperemic response is depicted in the micro-trend in FIG. 28 as the rapid increases and decreases in PNO.

A person of ordinary skill in the art will note that the macro trend is the gross increase in PNO during exercise, but within the macro trend there is a micro trend consisting of smaller increases/decreases in PNO. Together, these two trends work to regulate muscle blood flow.

Figure 29:
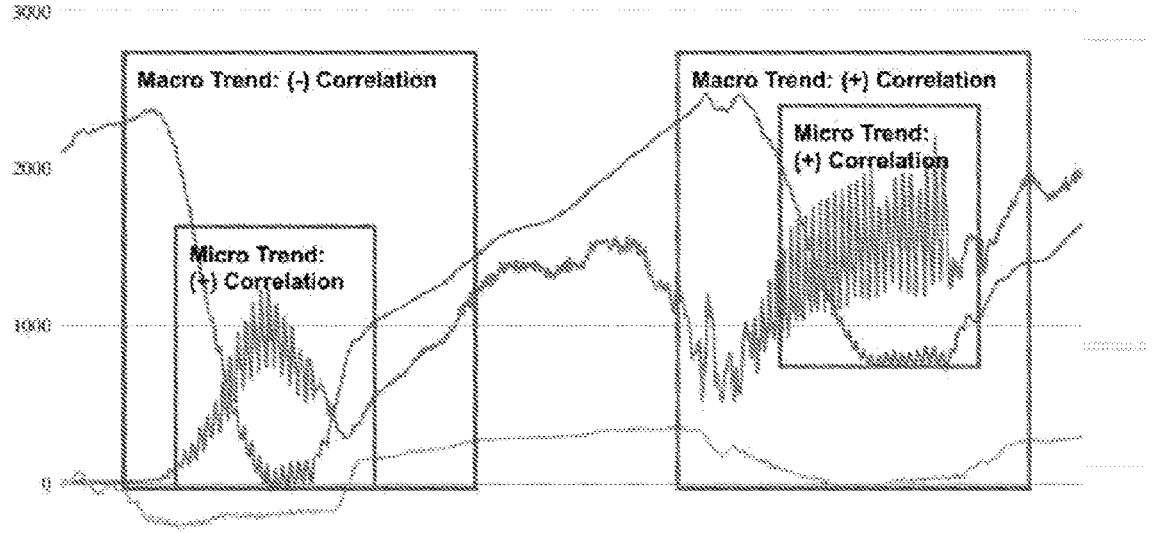
FIG. 29 depicts a graph demonstrating the effects of exercise on muscle oxygenation (SmO2) and s-nitrosothiols (PNO) with a (+) correlation nested within a (−) correlation as well as a (+) correlation nested within a (+) correlation according to some embodiments of the disclosure.

As seen in FIG. 29, there are also cases where the macro trend and micro trend show positive linear correlations, as would be the case when muscle contraction are having a stronger than usual impact on blood flow. As a result, the auto-regulatory response cannot be clearly observed. However, because linear correlations, whether positive or negative, are being examined, the PNO still increases.

In FIG. 29, there is a (+) correlation nested within a (−) correlation as well as a (+) correlation nested within a (+) correlation. While it is not possible to visually distinguish between the two, the possibility is worth mentioning (the second set has higher PNO for reasons other than the fact that it is a +/+ correlation).

Following a tissue injury, an injured person can believe the tissue injury has fully recovered, and full weight can be placed on the injured tissue and/or the injured body part is fully functional when in fact this tissue injury has not yet fully recovered. The determination for actual full tissue injury recovery can be made by comparing the Nitric Oxide levels from the injured limb and the opposing, uninjured limb of the same type (i.e., arms or legs). Based on the metrics described herein, the injured person can proceed with full activity with a reduced possibility of reinjury.

Example: Study

To establish the importance of SNOs, specifically SNO-Hb-βCys93, in clinically relevant measures of hypoxic vasodilation, mice expressing human Hb were utilized. The mice are depleted in SNO-Hb and show a number of cardiovascular deficits resulting from impairment of hypoxic vasodilation. In the study, the functional consequences of Cys93 SNO emulating a standard clinical protocol for reactive hyperemia: reoxygenation in gastrocnemius muscle (as measured by pO2 with a needle electrode) after five minutes of femoral artery occlusion was examined.

Figure 30A:
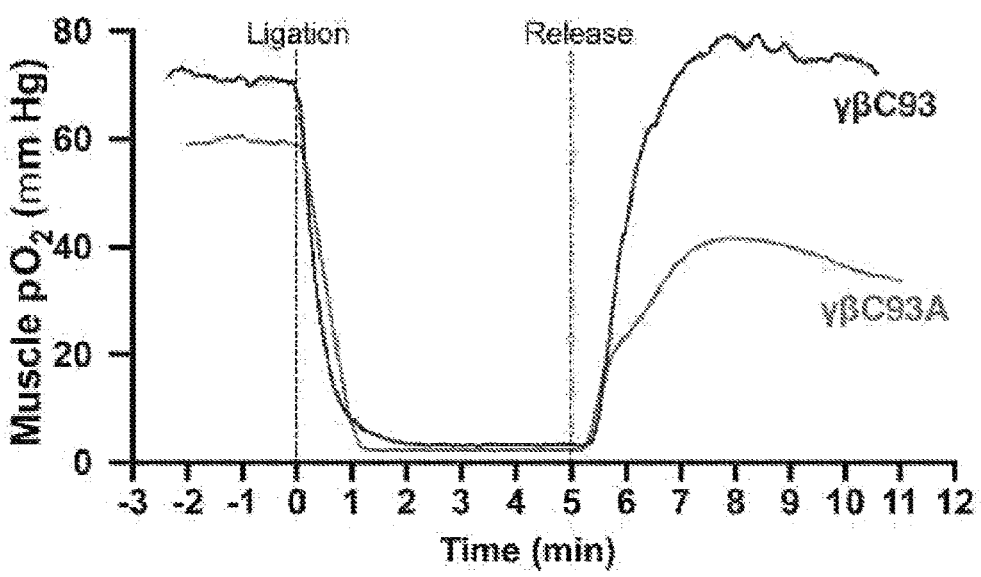
FIG. 30A depicts representative tracings from a control PC93 mouse and a corresponding βC93A mutant animal according to some embodiments of the disclosure.
Figures 30B, 30C:
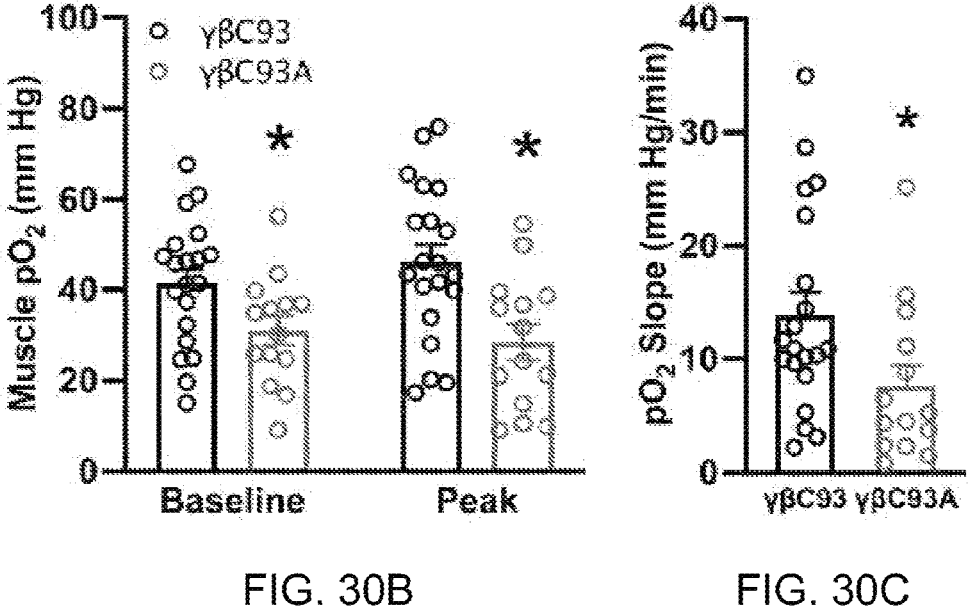
FIG. 30B depicts basal pO2 in gastrocnemius muscle from a control βC93 mouse and a corresponding βC93A mutant animal according to some embodiments of the disclosure.
FIG. 30C depicts a rate of post-occlusion recovery in muscle pO2 from a control βC93 mouse and a corresponding βC93A mutant animal according to some embodiments of the disclosure.

FIG. 30A depicts representative tracings from a control βC93 mouse and a corresponding βC93A mutant animal. In the βC93 mouse with normal hypoxic vasodilatory activity, the tissue pO2 response following release of the artery occlusion (i.e., restoration of femoral artery flow) was a rapid recovery that even overshot the baseline. In contrast, the βC93A animal exhibited a delayed response and muscle oxygenation did not return to baseline during the five minute post-release recording interval. Group data comparisons showed that basal pO2 in gastrocnemius muscle was significantly lower in the βC93A mice, as shown in FIG. 30B; p=0.032, consistent with our previous study. The group data comparisons additionally showed that the recovery of muscle pO2 after five minutes in βC93A mice was blunted compared to βC93 controls (46±17 vs. 28±15 mm Hg; p=0.004). The group data comparisons also showed that the rate of post-occlusion recovery in muscle pO2 was significantly reduced compared to that of γβC93 mice, at about half of the normal rate (0.23±0.15 vs. 0.13±0.11 mm Hg/sec, respectively), as shown in FIG. 30C; p=0.036. Thus SNO-Hb deficiency reduces the rate and overall efficiency of tissue oxygenation resulting from a brief interruption in blood flow.

RBC SNO levels were measured in age-matched healthy controls versus patients diagnosed with diseases characterized by systemic (i.e., heart failure and chronic obstructive pulmonary disease (COPD)) or peripheral (i.e., peripheral vascular disease and sickle cell disease) deficiencies in oxygenation: diabetic peripheral artery disease (PAD); heart failure with reduced ejection fraction (HF); COPD; and sickle cell disease (SCD). Specific inclusion criteria and disease status for each cohort are provided in the extended methods. 53 subjects, with 49 individuals completing the study (13 healthy, 13 PAD, 6 HF, 9 COPD, and 8 SCD), were enrolled.

RBCs were processed on site and SNO-Hb and iron-nitrosyl hb was quantified by Hg coupled photolysis-chemiluminescence within ~1 hour of procurement from the radial artery. Values from nine subjects were discarded due to an instrument malfunction (i.e., the diagnosis and the decision to discard those data were made by technical staff unaware of the patients' physiologic status). Results from the remaining samples are presented in FIGS. 31A-D.

Figure 31A:
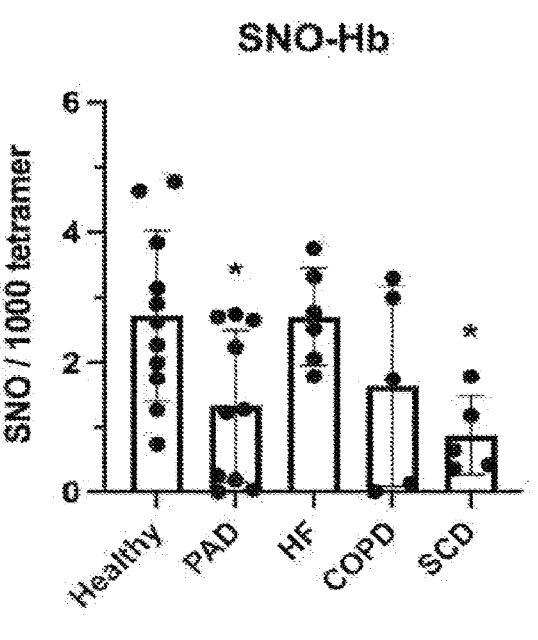
FIG. 31A depicts SNO-Hb isolated from fresh arterial blood for a patient group according to some embodiments of the disclosure.
Figure 31B:
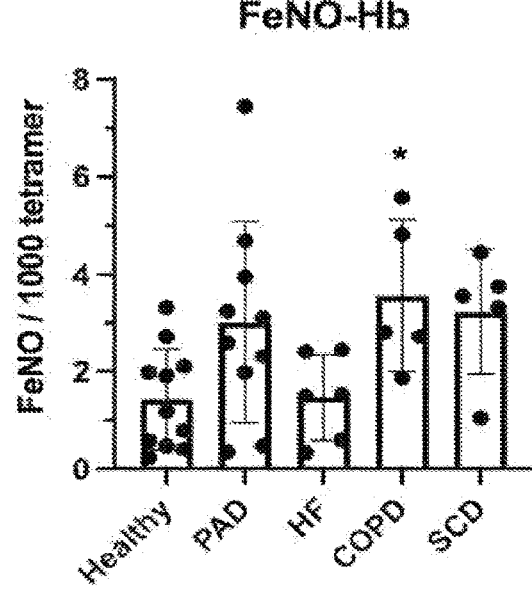
FIG. 31B depicts FeNO levels for a patient group according to some embodiments of the disclosure.
Figure 31C:
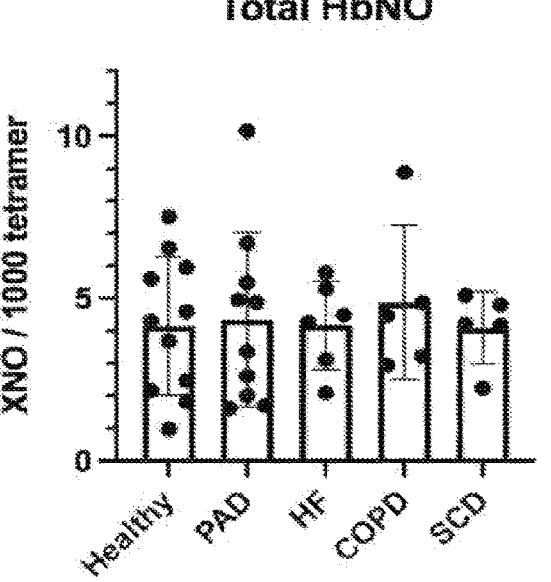
FIG. 31C depicts total HbNO for a patient group according to some embodiments of the disclosure.
Figure 31D:
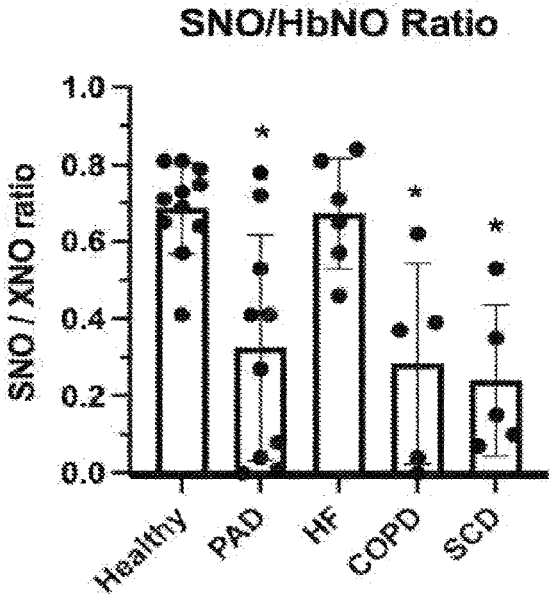
FIG. 31D depicts a ratio of SNO to total HbNO for a patient group according to some embodiments of the disclosure.

In the normal volunteers (n=10), arterial RBC SNO-Hb levels were 2.6±1.3 per 1000 Hb, as shown in FIG. 31A, a concentration similar to what was recorded in other groups of healthy subjects. SNO-Hb level in the HF cohort (n=5; 2.5±0.6 per 1000 Hb) and COPD cohort (n=5; 2.0±1.3) did not differ from controls. However, the amount of SNO-Hb in the blood from the PAD (n=11; 1.5±1.2) and SCD (n=5;

0.9±0.6) patients were significantly lower than in the normal controls (p<0.05). Levels of SNO-Hb can decline because of overall decreases in NO production or because of processing defects within the Hb molecule that prevent intramolecular transfer of NO from heme to thiol, as previously reported for SCD, PH, and for healthy subjects under hypoxia, reflected in increases in amounts of inactive FeNO. Notably, the total amount of NO bound to Hb (HbNO) did not differ from normal in any patient group, as shown in FIG. 31C. However, HbFeNO concentrations, as shown in FIG. 31B, were significantly higher than normal in the PAD, COPD, and SCD patient groups, reflecting a significant decline in the ratio of SNO to total HbNO in all groups except HF: from 0.69±0.13 and 0.67±0.16 in the normal volunteers and HF patients, respectively, to 0.36±0.30 in PAD, 0.36±0.22 in COPD, and 0.24±0.20 in SCD. Exploratory analysis of correlations between SNO-Hb and various clinical chemistry parameters was also conducted. FIG. 31C depicts total HbNO and FIG. 31D depicts a ratio of SNO to total HbNO for the identified patient group. Analyses of the data set, as shown in FIG. 33 (n=33), identified inverse correlations between plasma nitrite levels vs. SNO-Hb, and nitrite vs. the SNO-Hb/total HbNO ratio. Differences in SNO-Hb and FeNO levels, the ratio of SNO to total HbNO, and negative correlations between plasma nitrite and NO bioactivity are all suggestive of NO processing defects in the RBCs from PAD, COPD, and SCD patients.

The study sought to confirm the role of SNO-Hb in reactive hyperemia as demonstrated in βC93A mice. Following blood procurement, calf and foot tissue oxygenation were measured using a near-infrared spectroscopy (NIRS) device following brief periods of limb blood flow occlusion. Patients with SCD were excluded from this arm of the study due to the potential for leg ischemia to induce a vaso-occlusive crisis. Subjects in the other cohorts were placed semi-supine with inflatable cuffs wrapped around their upper thigh and lower calf near the ankle. Each cuff was rapidly inflated over one second to halt arterial blood flow (target pressure=systolic blood pressure+~130 mm Hg; max 300 mm Hg), and the occlusive period held for five minutes, before releasing the cuff pressure and measuring tissue oxygenation for five minutes. There was a five minute recovery interval between the two-cuff inflation/recording sessions, with the ankle cuff being used first with recording at the foot, and the thigh cuff being used second, with separate recordings at both foot and upper calf. Occlusion testing was conducted on 45 subjects, with the NIRS tracings analyzed off-line by individuals unaware of the subjects' disease status or RBC SNO levels. Thirteen of the resultant NIRS recordings were deemed uninterpretable by the independent analysis group due to leg motion and/or poor signal resolution and thus excluded, leaving data from 11 healthy. 8 PAD, 6 HF, and 7 COPD patients for comparative purposes.

Figure 32A:
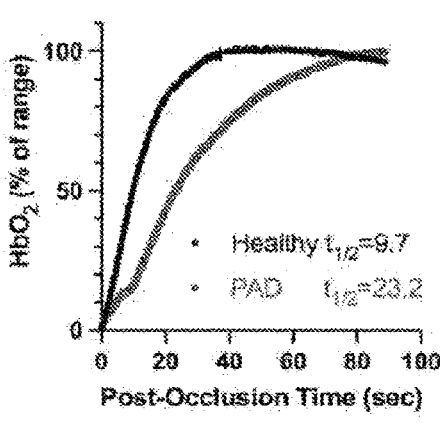
FIG. 32A depicts representee near-infrared sensor measurements of the recovery of Hb oxygenation over time in a healthy control and a PAD patient according to some embodiments of the disclosure.
Figure 32B:
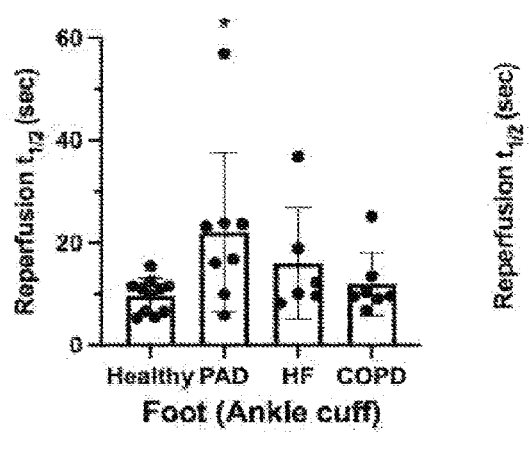
FIG. 32B depicts reperfusion recovery half-time in a patient group using a cuff at the ankle and measuring at the foot according to some embodiments of the disclosure.
Figure 32C:
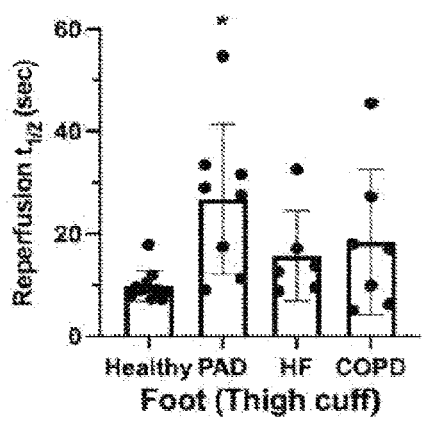
FIG. 32C depicts reperfusion recovery half-time in a patient group using a cuff at the thigh and measuring at the foot according to some embodiments of the disclosure.
Figure 32D:
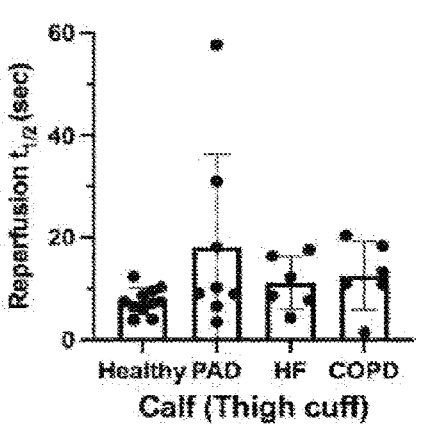
FIG. 32D depicts reperfusion recovery half-time in a patient group using a cuff at the thigh and measuring at the calf according to some embodiments of the disclosure.
Figure 32E:
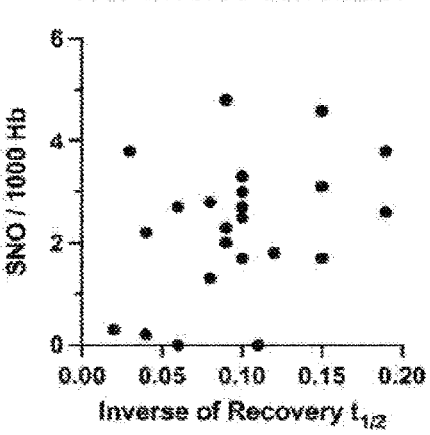
FIG. 32E depicts correlation of SNO-Hb level and recovery half-time according to some embodiments of the disclosure.

The experimental endpoint was half-time measured in seconds (t½) to restoration of tissue oxygenation (i.e., 50% return to baseline) and the findings are presented in FIGS. 32A-E. Representative foot tissue oxygenation recovery tracings from one healthy subject and one PAD patient are shown in FIG. 32A after release of the thigh cuff. The healthy subject had a robust and rapid re-oxygenation response with t½ of 10 sec, while the PAD patient exhibited a delayed tissue oxygenation response with a t½ of 22 seconds. This is very similar to the rapid restoration of tissue pO2 in the βC93 control mice following release of femoral artery occlusion versus slower recovery in βC93A mice, as shown in FIG. 30A. Quantified group data (mean±SD)

showing the t½ for foot re-oxygenation following ankle and thigh cuff occlusion and for calf re-oxygenation following thigh occlusion are presented in FIGS. 32B, 32C, and 32D, respectively. For all three measures, the healthy subjects recorded mean t½ values of approximately 10 seconds, consistent with previous studies. Importantly, as a group there was a direct correlation between SNO-Hb levels and reperfusion rate, as shown in FIG. 32E. Numerically higher mean t½ values were observed for all three patient groups, but the foot reperfusion half-times following ankle or cuff inflation significantly increased only in the PAD subject group. Further, there was a significant inverse correlation between foot re-perfusion t½ vs. SNO-Hb levels and vs. the SNO-Hb to total HbNO ratio but not vs. FeNO levels, as shown in FIG. 34, thus linking RBC SNO to reoxygenation response.

Microvascular blood flow is impaired in many clinical conditions resulting in tissue ischemia. However, drugs that increase blood flow do not improve tissue oxygenation. Also, clinical measures of blood flow have focused on the endothelial component, in particular NO, which plays no role in tissue oxygenation. On the other hand, there is strong evidence that blood flow governing tissue oxygenation is regulated by S-nitrosohemoglobin. Alternatively stated, blood flow subserving blood pressure is regulated by endothelial NO whereas blood flow regulating tissue oxygenation is controlled by RBC-SNO. Reactive hyperemia is the increase in blood flow following transient ischemia that occurs to restore tissue oxygenation. Whereas reactive hyperemia has been attributed to endothelial NO. RBC-SNO has a major role both vasodilatory and blood flow responses in mice. The current study expands that work to include direct measure of tissue oxygenation in both mice and humans. Importantly, the study demonstrates that SNO-Hb is required to oxygenate hypoxic tissues and that deficits in SNO-Hb lead to impairments in oxygenation. Moreover, levels of SNO-Hb in patients predict tissue oxygenation following a brief period of localized hypoxia indicating a first biomarker of microcirculatory blood flow.

The study presents a model of a 3-gas model for the respiratory cycle where O2/NO are loaded on to Hb simultaneously and SNO-Hb then releases vasodilatory SNO to adjust blood flow with tissue oxygen delivery. In the mutant mice unable to carry or dispense SNO from βCys93, tissue oxygenation is therefore broadly impaired. In addition to tissue hypoxia under basal conditions, mutant mice exhibit deficits in tissue oxygenation under global hypoxia and under regional ischemia, as shown as shown in FIG. 30B. Conversely, hypoxic conditions that impair oxygen loading, or otherwise impair the allosteric transition in Hb, also impair S-nitrosylation. This manifests either in terms of lower SNO-Hb levels or lower ratio of SNO-Hb to total HbNO, since NO still binds heme iron, only it cannot transfer to Cys93. Correspondingly, patients with disease states characterized by pathologies of oxygen (COPD, PAD, and SCD) exhibited lower levels of SNO-Hb and lower SNO/HbNO, as shown in FIGS. 31A-D, confirming previous reports. Predictably, the ratio of SNO-Hb to total Hb-associated NO (SNO-Hb plus Hb FeNO; total HbNO), indicative of accumulation of inactive FeNO, was a more sensitive measure of loss of bioactivity than measures of SNO-Hb alone. Thus, NO/SNO processing defects are observed in multiple diseases characterized by deficient tissue oxygenation and may be causally linked by a shared inability of Hb to convert FeNO to SNO-βCys93-Hb. By the same token, we found that the ratios of SNO-Hb to nitrite and of SNO-Hb/HbNO to blood nitrite are actually inversely correlated, consistent with prior findings that higher nitrite blocks SNO-Hb formation, as shown in FIG. 33. It follows that nitrite levels are unrelated to blood flow or tissue oxygenation.

Patients with PAD have well characterized microvascular dysfunction. When tested for recovery from transient ischemia of the lower limb, reperfusion in this cohort was significantly delayed, as shown in FIGS. 32A-E, and in all cases the t½ to reoxygenation was longer compared to the healthy controls. Importantly, while statistical differences in t½ to reoxygenation were not observed in other cohorts, a significant correlation was found between SNO-Hb levels and oxygenation rate across all patient cohorts. Taken together, with the genetic validation in mice, these results suggest that SNO-Hb is a key driver of blood flow auto-regulation whereby tissue blood flow controls tissue oxygenation. These findings have multiple clinical implications. Reactive hyperemia, previously viewed as a measure of endothelial function, has a significant RBC SNO component. More generally, endothelial NO and RBC SNO have different roles, the former in vascular health and the latter in tissue health. The results add to the body of research pointing to RBC SNO-Hb as a biomarker of tissue oxygenation status especially since SNO-Hb was directly correlated with reperfusion rate. Furthermore, the study shows that reactive hyperemia testing is a useful measure of SNO-Hb functionality in patient populations. The ability to enhance RBC SNO may improve tissue oxygenation and could have widespread clinical utility. In certain embodiments, exercise is used for benefits of oxygenation in a subject having a disease status. For example, the subject may have heart disease, vascular disease, diabetes, cancer, frailty and/or muscle disorders (e.g., muscle metabolism dysregulation) and PNO would be diagnostic, prognostic and/or potentially therapeutic.

Specific details are given in the above description to provide a thorough understanding of the embodiments. However, it is understood that the embodiments can be practiced without these specific details. For example, physical components can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps, and means described above can be done in various ways. For example, these techniques, blocks, steps, and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed but could have additional steps not included in the figure. A process can correspond to a method, a function, a procedure, a subroutine, a subprogram, etc. When a process corresponds to a function, its termina-tion corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine-readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine-readable mediums for storing information. The term "machine-readable medium" includes but is not limited to portable or fixed storage devices, optical storage devices, wireless channels, and/or various other storage mediums capable of storing that contain or carry instruction(s) and/or data.

In the preceding description, specific details have been set forth in order to provide a thorough understanding of example implementations of the systems and methods described in the disclosure. However, it will be apparent that various implementations may be practiced without these specific details. For example, circuits, systems, networks, processes, and other components may be shown as components in block diagram form in order not to obscure the example implementations in unnecessary detail. In other instances, well-known circuits, processes, algorithms, structures, and techniques may be shown without unnecessary detail in order to avoid obscuring the examples. The description of the example implementations will provide those skilled in the art with an enabling description for implementing an example embodiment, but it should be understood that various changes may be made in the function and arrangement of elements without departing from the spirit and scope of the disclosure. Accordingly, the present disclosure is intended to embrace all such alterations, modifications, and variations that fall within the scope of any appended claims.

The invention claimed is:

1. A system comprising:

at least one light source configured to illuminate a region of interest of a subject;

at least one light sensor configured to non-invasively measure reflected light within the region of interest of the subject;

at least one processor in communication with the sensor; and at least one non-transitory computer readable medium storing machine-readable instructions that, when executed by the at least one processor, cause the at least one processor to perform processing comprising:

receiving at least one measured value of light from the at least one light sensor;

determining an irradiance distribution for the region of interest of the subject using the at least one measured value and at least a parameter generated by a stochastic model as inputs;

calculating, from the irradiance distribution, at least one characteristic attenuation coefficient for at least one wavelength of the light; and based on the at least one characteristic attenuation coefficient and the at least one measured value of light, determining at least one physical characteristic of the region of interest of the subject.

2. The system of claim 1, wherein the at least one physical characteristic includes one or more of a water measurement, an internal training load, an oxygenated hemoglobin measurement, a deoxygenated hemoglobin measurement, a total hemoglobin measurement, a blood volume measurement, a muscle oxygenation, a muscle oxygen consumption, an active nitric oxide measurement, an active s-nitrosothiols measurement, an adipose thickness, and a melanin content.

3. The system of claim 1, wherein the at least one physical characteristic includes a combination of a pulse oximetry and nitric oxide.

4. The system of claim 1, wherein the at least one measured value of light includes a time series of measurements and the at least one physical characteristic includes a time series of characteristics, the processing further comprising:

generating a value representing an endogenous S-nitrosothiol content of tissue within the region of interest from the time series of characteristics; and storing the value representing the endogenous S-nitrosothiol content of tissue within the region of interest in the non-transitory computer readable medium.

5. The system of claim 4, wherein the time series of characteristics includes a time series of oxygen saturation measurements and a time series of blood volume measurements.

6. The system of claim 5, wherein the generating of the value comprises:

determining a linearity of relationship between the time series of blood volume measurements and the time series of oxygen saturation measurements and provides a set of parameters; and generating the value representing the endogenous S-nitrosothiol content of tissue within the region of interest from the set of parameters.

7. The system of claim 6, wherein the generating of the value comprises:

using a linear regression model to provide a best-fit line defined by the set of parameters, the set of parameters including a slope of the best-fit line; and generating the value representing the endogenous S-nitrosothiol content of tissue within the region of interest from the slope of the best-fit line.

8. The system of claim 1, wherein the at least one processor is configured to perform the determining of the at least one physical characteristic during one of a period of exercise by the subject or a time period immediately after the period of exercise by the subject.

9. The system of claim 1, wherein the processing further comprises displaying, by at least one display device in communication with the at least one processor, at least one indication of the at least one physical characteristic.

10. The system of claim 9, wherein the at least one indication includes guidance related to an internal training load of the subject.

11. The system of claim 10, wherein the guidance is directed towards decreasing a risk of injury.

12. The system of claim 9, wherein the at least one indication includes information related to a muscle oxygen consumption of the subject.

13. The system of claim 12, wherein the information includes a VO2 indication.

14. The system of claim 1, wherein the stochastic model comprises a three-dimensional model with six degrees of freedom.

15. The system of claim 14, wherein the six degrees of freedom include location coordinates and direction cosines.

16. A method comprising:

illuminating, by at least one light source a region of interest of a subject;

detecting, by at least one light sensor, reflected light from the region of interest of the subject;

receiving, by at least one processor, at least one measured value of light from the at least one light sensor;

determining, by the at least one processor, an irradiance distribution for the region of interest of the subject using the at least one measured value and at least a parameter generated by a stochastic model as inputs;

calculating, by the at least one processor, from the irradiance distribution, at least one characteristic attenuation coefficient for at least one wavelength of the light; and based on the at least one characteristic attenuation coefficient and the at least one measured value of light, determining, by the at least one processor, at least one physical characteristic of the region of interest of the subject.

17. The method of claim 16, wherein the at least one physical characteristic includes one or more of a water measurement, an internal training load, an oxygenated hemoglobin measurement, a deoxygenated hemoglobin measurement, a total hemoglobin measurement, a blood volume measurement, a muscle oxygenation, a muscle oxygen consumption, an active nitric oxide measurement, an active s-nitrosothiols measurement, an adipose thickness, and a melanin content.

18. The method of claim 16, wherein the at least one physical characteristic includes a combination of a pulse oximetry and nitric oxide.

19. The method of claim 16, wherein the at least one measured value of light includes a time series of measurements and the at least one physical characteristic includes a time series of characteristics, the method further comprising:

generating, by the at least one processor, a value representing an endogenous S-nitrosothiol content of tissue within the region of interest from the time series of characteristics; and storing, by the at least one processor, the value representing the endogenous S-nitrosothiol content of tissue within the region of interest in a non-transitory computer readable medium.

20. The method of claim 19, wherein the time series of characteristics includes a time series of oxygen saturation measurements and a time series of blood volume measurements.

21. The method of claim 20, wherein the generating of the value comprises:

determining a linearity of relationship between the time series of blood volume measurements and the time series of oxygen saturation measurements and provides a set of parameters; and generating the value representing the endogenous S-nitrosothiol content of tissue within the region of interest from the set of parameters.

22. The method of claim 21, wherein the generating of the value comprises:

using a linear regression model to provide a best-fit line defined by the set of parameters, the set of parameters including a slope of the best-fit line; and generating the value representing the endogenous S-nitrosothiol content of tissue within the region of interest from the slope of the best-fit line.

23. The method of claim 16, wherein the determining of the at least one physical characteristic is performed during one of a period of exercise by the subject or a time period immediately after the period of exercise by the subject.

24. The method of claim 16, further comprising displaying, by at least one display device in communication with the at least one processor, at least one indication of the at least one physical characteristic.

25. The method of claim 24, wherein the at least one indication includes guidance related to an internal training load of the subject.

26. The method of claim 25, wherein the guidance is directed towards decreasing a risk of injury.

27. The method of claim 24, wherein the at least one indication includes information related to a muscle oxygen consumption of the subject.

28. The method of claim 27, wherein the information includes a VO2 indication.

29. The method of claim 16, wherein the stochastic model comprises a three-dimensional model with six degrees of freedom.

30. The method of claim 29, wherein the six degrees of freedom include location coordinates and direction cosines.

* * * * *